US010376320B2

(12) United States Patent
Harlev et al.

(10) Patent No.: US 10,376,320 B2
(45) Date of Patent: Aug. 13, 2019

(54) ANATOMICAL MODEL GENERATION

(71) Applicant: Affera, Inc., Watertown, MA (US)

(72) Inventors: Doron Harlev, Brookline, MA (US); Geoffrey Peter Wright, Boston, MA (US)

(73) Assignee: Affera, Inc., Watertown, MA (US)

( * ) Notice: Subject to any disclaimer, the term of this patent is extended or adjusted under 35 U.S.C. 154(b) by 0 days.

(21) Appl. No.: 15/592,815

(22) Filed: May 11, 2017

(65) Prior Publication Data

US 2017/0325891 A1 Nov. 16, 2017

Related U.S. Application Data

(60) Provisional application No. 62/334,577, filed on May 11, 2016, provisional application No. 62/338,105, (Continued)

(51) Int. Cl.
*A61B 5/00* (2006.01)
*A61B 5/06* (2006.01)
(Continued)

(52) U.S. Cl.
CPC .............. *A61B 34/10* (2016.02); *A61B 5/742* (2013.01); *A61B 18/1492* (2013.01);
(Continued)

(58) Field of Classification Search
CPC ....... G06T 2210/41; G06T 2207/30048; G06T 2207/10072; G06T 2207/30101;
(Continued)

(56) References Cited

U.S. PATENT DOCUMENTS

| 5,391,199 A | 2/1995 | Ben-Haim |
| 5,433,198 A | 7/1995 | Desai |

(Continued)

FOREIGN PATENT DOCUMENTS

| EP | 1793349 A2 | 6/2007 |
| EP | 1837828 | 9/2007 |

(Continued)

OTHER PUBLICATIONS

Gelas, Arnaud, "Surface Meshes Smoothing", Feb. 20, 2009 , 6 Pages.

(Continued)

*Primary Examiner* — Jeffrey J Chow
(74) *Attorney, Agent, or Firm* — Perkins Coie LLP

(57) ABSTRACT

Devices, systems, and methods of the present disclosure are directed to generating three-dimensional surface representations of an anatomic structure such as a heart cavity. More specifically, a three-dimensional surface representation of the anatomic structure is constrained relative to one or more anchor portions corresponding to received input regarding the location of anatomic features of the anatomic structure. The resulting three-dimensional surface representation includes salient features of the anatomic structure and, therefore, can be useful as visualization tool during any of various different medical procedures, including, for example, cardiac ablation.

18 Claims, 11 Drawing Sheets

Related U.S. Application Data filed on May 18, 2016, provisional application No. 62/393,876, filed on Sep. 13, 2016.

(51) Int. Cl.

| | |
|---|---|
| *A61B 8/12* | (2006.01) |
| *A61B 18/00* | (2006.01) |
| *A61B 18/14* | (2006.01) |
| *A61B 34/00* | (2016.01) |
| *A61B 34/10* | (2016.01) |
| *A61B 34/20* | (2016.01) |
| *A61B 5/042* | (2006.01) |
| *A61B 90/00* | (2016.01) |
| *G06T 17/00* | (2006.01) |
| *G06T 17/20* | (2006.01) |
| *G06T 19/20* | (2011.01) |
| *G16H 50/50* | (2018.01) |

(52) U.S. Cl.
CPC .............. *A61B 34/20* (2016.02); *A61B 34/25* (2016.02); *G06T 17/00* (2013.01); *G06T 17/20* (2013.01); *G06T 19/20* (2013.01); *G16H 50/50* (2018.01); *A61B 5/042* (2013.01); *A61B 5/062* (2013.01); *A61B 5/063* (2013.01); *A61B 5/6843* (2013.01); *A61B 8/12* (2013.01); *A61B 2018/00642* (2013.01); *A61B 2018/00839* (2013.01); *A61B 2018/00875* (2013.01); *A61B 2034/104* (2016.02); *A61B 2034/105* (2016.02); *A61B 2034/2051* (2016.02); *A61B 2034/2063* (2016.02); *A61B 2090/064* (2016.02); *G06T 2200/24* (2013.01); *G06T 2210/41* (2013.01); *G06T 2219/004* (2013.01)

(58) Field of Classification Search
CPC . G06T 17/00; G06T 7/11; G06T 2207/30004; G06T 15/08; G06T 2207/20124; G06T 2207/10132; G06T 2207/30021; G06T 2207/10068; G06T 2207/10136; G06T 2207/30061; G06T 2207/10028; G06T 2207/30028; G06T 15/00; G06T 2207/30016; G06F 19/3437; G06F 19/12; A61M 2025/0166
See application file for complete search history.

(56) References Cited

U.S. PATENT DOCUMENTS

| | | | |
|---|---|---|---|
| 5,447,529 A | 9/1995 | Marchlinski et al. | |
| 5,655,535 A | 8/1997 | Friemel et al. | |
| 5,687,737 A | 11/1997 | Branham et al. | |
| 5,797,849 A | 8/1998 | Vesely et al. | |
| 5,820,568 A | 10/1998 | Willis et al. | |
| 5,889,524 A | 3/1999 | Sheehan et al. | |
| 6,175,655 B1 | 1/2001 | George, III et al. | |
| 6,256,038 B1 | 7/2001 | Krishnamurthy | |
| 6,271,856 B1 | 8/2001 | Krishnamurthy | |
| 6,377,865 B1 | 4/2002 | Edelsbrunner et al. | |
| 6,443,894 B1 | 9/2002 | Sumanaweera et al. | |
| 6,968,299 B1 | 11/2005 | Bernardini et al. | |
| 7,023,432 B2 | 4/2006 | Fletcher et al. | |
| 7,155,042 B1* | 12/2006 | Cowan .................. | A61B 5/055 382/128 |
| 7,365,745 B2 | 4/2008 | Olson | |
| 8,786,594 B2 | 7/2014 | Kushwaha et al. | |
| 9,245,382 B2 | 1/2016 | Zhou et al. | |
| 9,256,980 B2 | 2/2016 | Kirk | |
| 9,311,744 B2 | 4/2016 | Wu et al. | |
| 9,613,291 B2 | 4/2017 | Wu et al. | |
| 2006/0159323 A1 | 7/2006 | Sun et al. | |
| 2006/0241445 A1 | 10/2006 | Altmann et al. | |
| 2009/0076476 A1 | 3/2009 | Barbagli et al. | |
| 2009/0264742 A1* | 10/2009 | Markowitz .......... | A61B 5/0422 600/424 |
| 2010/0053208 A1* | 3/2010 | Menningen ............ | A61B 6/032 345/619 |
| 2011/0152684 A1 | 6/2011 | Altmann et al. | |
| 2012/0004540 A1 | 1/2012 | Liu et al. | |
| 2013/0129170 A1* | 5/2013 | Zheng .................. | G06T 7/0079 382/131 |
| 2013/0241929 A1 | 9/2013 | Massaeawa et al. | |
| 2015/0018698 A1* | 1/2015 | Safran ..................... | G06F 17/11 600/508 |
| 2016/0196666 A1* | 7/2016 | Venkatraghavan ..... | G06T 7/254 382/130 |
| 2016/0242855 A1* | 8/2016 | Fichtinger .............. | A61B 34/20 |
| 2016/0275653 A1* | 9/2016 | Ross ...................... | G06T 5/002 |
| 2016/0367168 A1* | 12/2016 | Malinin ................. | A61B 5/066 |
| 2017/0245936 A1* | 8/2017 | Kanade .................... | A61B 5/06 |
| 2017/0301124 A1* | 10/2017 | Dala-Krishna ......... | G06T 13/20 |

FOREIGN PATENT DOCUMENTS

| | | |
|---|---|---|
| EP | 2332461 A1 | 6/2011 |
| WO | 2005022468 A1 | 3/2005 |
| WO | WO-2017197114 | 11/2017 |

OTHER PUBLICATIONS

ISA, "PCT Application No. PCT/US17/32160 International Search Report and Written Opinion dated Aug. 21, 2017", 10 pages.

Lounsbery, Michael et al., "Parametric Surface Interpolation", IEEE Computer Graphics and Applications 12.5 (1992) Sep. 1992, pp. 45-52.

Schroeder, William et al., "Flying Edges: A High-Performance Scalable Isocontouring Algorithm", IEEE Xplore, Oct. 2015, 8 pages.

Wang, Jianning et al., "A Hole-Filling Strategy for Reconstruction of Smooth Surfaces in Range Images", Computer Graphics and Image Processing, 2003. SIBGRAPI 2003. XVI Brazilian Symposium on. IEEE, Oct. 2003, 8 pages.

Bernardini, Fausto et al., "The Ball-Pivoting Algorithm for Surface Reconstruction", IEEE transactions on visualization and computer graphics 5.4 (1999), Oct. 1999, pp. 349-359.

Chen, Yang et al., "Description of Complex Objects from Multiple Range Images Using an Inflating Balloon Model", Computer Vision and Image Understanding 61.3, May 1995, pp. 325-334.

Lempitsky, Victor, "Surface Extraction from Binary Volumes with Higher-Order Smoothness", Computer Vision and Pattern Recognition (CVPR), 2010 IEEE Conference on. IEEE, Jun. 2010, 6 Pages.

Elfes, Alberto, "Using Occupancy Grids for Mobile Robot Perception and Navigation", Computer, vol. 22, Issue: 6, Jun. 1989, pp. 46-57.

Zhao, Hong-Kai et al., "Fast Surface Reconstruction Using the Level Set Method", Variational and Level Set Methods in Computer Vision, 2001. Proceedings. IEEE Workshop on. IEEE, Jul. 2001, 8 pages.

Gelas, Arnaud et al., "Surface Meshes Smoothing", Insight Journal. Feb. 20, 2009, 6 Pages.

Liang, Jian et al., "Robust and Efficient Implicit Surface Reconstruction for Point Clouds Based on Convexified Image Segmentation", Journal of Scientific Computing 54.2-3, 2013, pp. 577-602.

Kazhdan, Michael et al., "Poisson Surface Reconstruction", Eurographics Symposium on Geometry Processing, 2006, 10 Pages.

Davis, James et al., "Filling holes in complex surfaces using volumetric diffusion", 3D Data Processing Visualization and Transmission, 2002. Proceedings. First International Symposium on. IEEE, 2002, 6 Pages.

Carr, J. C. et al., "Reconstruction and Representation of 3D Objects with Radial Basis Functions", Proceedings of the 28th annual conference on Computer graphics and interactive techniques. ACM, 2001, 10 Pages.

(56) References Cited

OTHER PUBLICATIONS

Curless, Brian et al., "A Volumetric Method for Building Complex Models from Range Images", Proceedings of the 23rd annual conference on Computer graphics and interactive techniques. ACM, 1996, 10 Pages.
Sethian, J.A., "Level Set Methods and Fast Marching Methods", Cambridge University Press, 1996, 21 Pages.

* cited by examiner

ANATOMICAL MODEL GENERATION

CROSS-REFERENCE TO RELATED APPLICATIONS

This application claims the benefit under 35 U.S.C. § 119(e) of U.S. Prov. App. No. 62/334,577, filed May 11, 2016, U.S. Prov. App. No. 62/338,105, filed May 18, 2016, and U.S. Prov. App. No. 62/393,876, filed Sep. 13, 2016, with the entire contents of each of these applications hereby incorporated herein by reference.

BACKGROUND

Three-dimensional models can be used to assist in the placement or use of a device when such placement or use is not easily observable or practical. For example, in medical procedures, three-dimensional models are used to assist in the placement and use of medical devices for diagnosis or treatment of patients. An example of such a medical procedure carried out with the assistance of a three-dimensional model is the use of a catheter to deliver radio frequency ("RF") ablation to form lesions that interrupt abnormal conduction in cardiac tissue, thus terminating certain arrhythmias in the heart.

SUMMARY

The present disclosure is directed to devices, systems, and methods of generating an accurate three-dimensional model of an anatomic structure of a patient to facilitate, for example, moving a medical device through the anatomic structure during a medical procedure in which the three-dimensional model is used to visualize the medical device in the anatomic structure. For example, the systems and methods of the present disclosure can be used to generate a three-dimensional model based on input (e.g., from a physician) of anchor portions corresponding to the position of anatomic features of the anatomic structure. As a more specific example, the systems and methods of the present disclosure can be used to generate a three-dimensional surface representation of the anatomic structure, with the three-dimensional surface representation constrained relative to one or more anchor portions identified on a three-dimensional data structure. Because the constraint imposed by the one or more anchor portions can change the shape of the three-dimensional surface representation and, thus, can have the appearance of changing the position of tissue in a visual representation of the three-dimensional surface representation, the constraint imposed by the anchor portions is sometimes referred to herein as "pinch." More generally, the devices, systems, and methods of the present disclosure can provide a physician with a greater amount of control over a three-dimensional model of an anatomic structure and, additionally or alternatively, can represent salient features of the anatomic structure in greater detail than is typically achievable in a three-dimensional model built based solely on an incomplete or uncertain data set of known locations of a medical device in an anatomic structure.

According to one aspect, a method includes receiving a plurality of location signals, each received location signal indicative of a respective location of a medical device in an anatomic structure of a patient, forming a three-dimensional data structure representing locations, within the anatomic structure, visited by the medical device at the locations corresponding to the plurality of location signals, receiving one or more anchor portions representing locations relative to the anatomic structure, and generating a three-dimensional surface representation of the anatomic structure of the patient, the three-dimensional surface representation of the anatomic structure of the patient constrained relative to the one or more anchor portions and to contain at least a portion of the three-dimensional data structure.

In certain implementations, the method can further include displaying, on a graphical user interface, at least one of a two-dimensional projection of the three-dimensional data structure, the one or more anchor portions, and a two-dimensional projection of the three-dimensional surface representation.

In some implementations, receiving the one or more anchor portions representing locations relative to the anatomic structure can include receiving, from one or more sensors disposed on the medical device, a signal indicative of contact between the medical device and tissue of the anatomic structure. The signal indicative of contact can be, for example, indicative of a blood-tissue boundary of the anatomic structure of the patient. Additionally, or alternatively, the signal indicative of contact can include one or more of: a change in impedance detected by one or more electrodes of the medical device, a force detected by a force sensor of the medical device, an ultrasound signal of an ultrasound sensor of the medical device, a deformation of at least a portion of the medical device, and an amplitude derived from an electrogram detected by one or more electrodes of the medical device.

In certain implementations, receiving the one or more anchor portions can include receiving an input command from a user.

In some implementations, receiving the one or more anchor portions can include identifying a subset of the three-dimensional data structure.

In certain implementations, receiving the one or more anchor portions can include receiving a respective confidence level associated each of the one or more anchor portions, and constraining the three-dimensional surface representation relative to the one or more anchor portions is based on the respective confidence level associated with each of the one or more anchor portions.

In some implementations, the method can further include representing, on a graphical user interface, the one or more anchor portions as annotations on the three-dimensional surface representation of the anatomic structure.

In certain implementations, the method can further include representing, on a graphical user interface, the one or more anchor portions as annotations on the three-dimensional data structure.

In some implementations, the method can further include determining whether the one or more anchor portions have been modified and, based on whether the one or more anchor portions have been modified, repeating the generating step. Determining whether the one or more anchor portions have been modified can include, for example, determining whether one or more of previously identified anchor portions have been removed.

In certain implementations, the three-dimensional surface representation of the anatomic structure can be a continuous mesh.

According to another aspect, a method includes forming a three-dimensional data structure based on received locations of a tip section of a cardiac catheter in a heart cavity of a patient, receiving one or more anchor portions representing locations relative to the heart cavity, and generating a three-dimensional surface representation of the heart cavity of the patient, the surface representation of the heart cavity of the patient constrained relative to the anchor portions and to contain at least a portion of the three-dimensional data structure.

In some implementations, the method can further include displaying, on a graphical user interface, at least one of a two-dimensional projection of the three-dimensional data structure, the one or more anchor portions, and a two-dimensional projection of the generated three-dimensional surface representation.

In certain implementations, receiving the one or more anchor portions on the three-dimensional data structure can include receiving one or more location signals indicative of one or more respective locations of the cardiac catheter in the heart cavity.

In some implementations, receiving the one or more anchor portions can include receiving, from a sensor disposed on the cardiac catheter, a signal indicative of a blood-tissue boundary of the heart cavity of the patient. The signal corresponding to the blood-tissue boundary can include one or more of: a change in impedance detected by one or more electrodes of the cardiac catheter, a force detected by a force sensor of the cardiac catheter, an ultrasound signal of an ultrasound sensor of the cardiac catheter, and a deformation of at least a portion of the cardiac catheter, and an amplitude derived from an electrogram detected by one or more electrodes of the cardiac catheter.

In certain implementations, receiving the one or more anchor portions on the three-dimensional data structure can include receiving an input command from a user interface.

In some implementations, the method can further include representing, on a graphical user interface, the one or more anchor portions as annotations on the three-dimensional surface representation of the heart cavity.

According to still another aspect, a non-transitory, computer-readable storage medium has stored thereon computer executable instructions for causing one or more processors to: receive a plurality of location signals, each received location signal indicative of a respective location of a medical device in an anatomic structure of a patient; form a three-dimensional data structure representing volumes, within the anatomic structure, occupied by the medical device at the locations corresponding to the plurality of location signals; receive one or more anchor portions representing locations relative to the anatomic structure; and generate a three-dimensional surface representation of the anatomic structure of the patient, the three-dimensional surface representation of the anatomic structure of the patient constrained relative to the one or more anchor portions and containing at least a portion of the three-dimensional data structure.

Implementations can include one or more of the following advantages.

In certain implementations, a three-dimensional surface representation of an anatomic structure can be based on one or more anchor portions. For example, the three-dimensional surface representation of the anatomic structure can be constrained to pass near the one or more anchor portions and/or to pass near a fixed position relative to the one or more anchor portions. By imposing such conditions, the three-dimensional surface representation can accurately represent an anatomic structure such as, for example, an anatomic structure with local concavities along a generally convex shape. Such accurate representation can be particularly advantageous for proper manipulation of a catheter for the accurate placement of lesions in the heart, such as placement of lesions in the carina between pulmonary veins.

Further, constraining the three-dimensional representation relative to one or more anchor portions can facilitate generating an accurate representation of the anatomic structure based on relatively few data points (e.g., an incomplete or uncertain data set) while still providing a useful representation of salient anatomic features of the anatomic structure. Thus, for example, constraining the three-dimensional surface representation relative to one or more anchor portions can facilitate building a useful depiction of the anatomic structure in less time than would ordinarily be required to achieve the same level of detail in a model built based on catheter position alone. Additionally, or alternatively, constraining the three-dimensional surface representation relative to one or more anchor portions can facilitate shaping the three-dimensional surface representation independently of other parameters used to form the three-dimensional surface representation (e.g., tightness of a surface mesh).

In some implementations, one or more anchor portions can be based on feedback from one or more sensors on a medical device within an anatomic structure. In certain implementations, the one or more anchor portions can be based on input from the physician. Thus, for example, the one or more anchor portions can be based on a useful combination of physician input and feedback from one or more sensors of a medical device positioned within the anatomic structure. Such a combination can be useful for providing insights into the shape of the anatomic structure, while providing the physician with the ability to verify and, if necessary, override feedback from the one or more sensors.

Other aspects, features, and advantages will be apparent from the description and drawings, and from the claims.

BRIEF DESCRIPTION OF THE DRAWINGS

Like reference symbols in the various drawings indicate like elements.

DETAILED DESCRIPTION

The present disclosure is generally directed to devices, systems, and methods of generating a three-dimensional surface representation of an anatomic structure of a patient. More specifically, the three-dimensional surface representation can accurately represent local anatomic features of the anatomic structure, while being based on an incomplete or uncertain data set, by constraining (e.g., pinching) the three-dimensional surface representation relative to the one or more anchor portions. For at least this reason, the three-dimensional surface representations generated according to the devices, systems and methods of the present disclosure can be generated efficiently and, in use, can be useful for facilitating visualization of a position of a medical device (e.g., a catheter) during a medical procedure (e.g., diagnosis and/or treatment) being performed on the anatomic structure.

It should be appreciated that, unless otherwise specified or made clear from the context, the systems and methods of the present disclosure can be used for any of various different medical procedures, such as procedures performed on a hollow anatomic structure of a patient, and, more specifically, in a hollow anatomic structure, in which direct visual access to the medical procedure is impractical and/or is improved by the use of a model of the anatomic structure. Thus, for example, the systems and methods of the present disclosure can be used to facilitate visualization of a catheter inserted into a heart cavity as part of a medical treatment associated with diagnosis, treatment, or both of a cardiac condition (e.g., cardiac arrhythmia). Additionally, or alternatively, the systems and methods of the present disclosure can be used in one or more medical procedures associated with interventional pulmonology, brain surgery, or sinus surgery (e.g., sinuplasty).

As used herein, the term "physician" shall be understood to include any type of medical personnel who may be performing or assisting a medical procedure and, thus, is inclusive of a doctor, a nurse, a medical technician, other similar personnel, and any combination thereof. Additionally, or alternatively, as used herein, the term "medical procedure" shall be understood to include any manner and form of diagnosis, treatment, or both, inclusive of any preparation activities associated with such diagnosis, treatment, or both. Thus, for example, the term "medical procedure" shall be understood to be inclusive of any manner and form of movement or positioning of a medical device in an anatomic chamber.

As used herein, the term "patient" should be considered to include any mammal, including a human, upon which a medical procedure is being performed.

Figure 1:
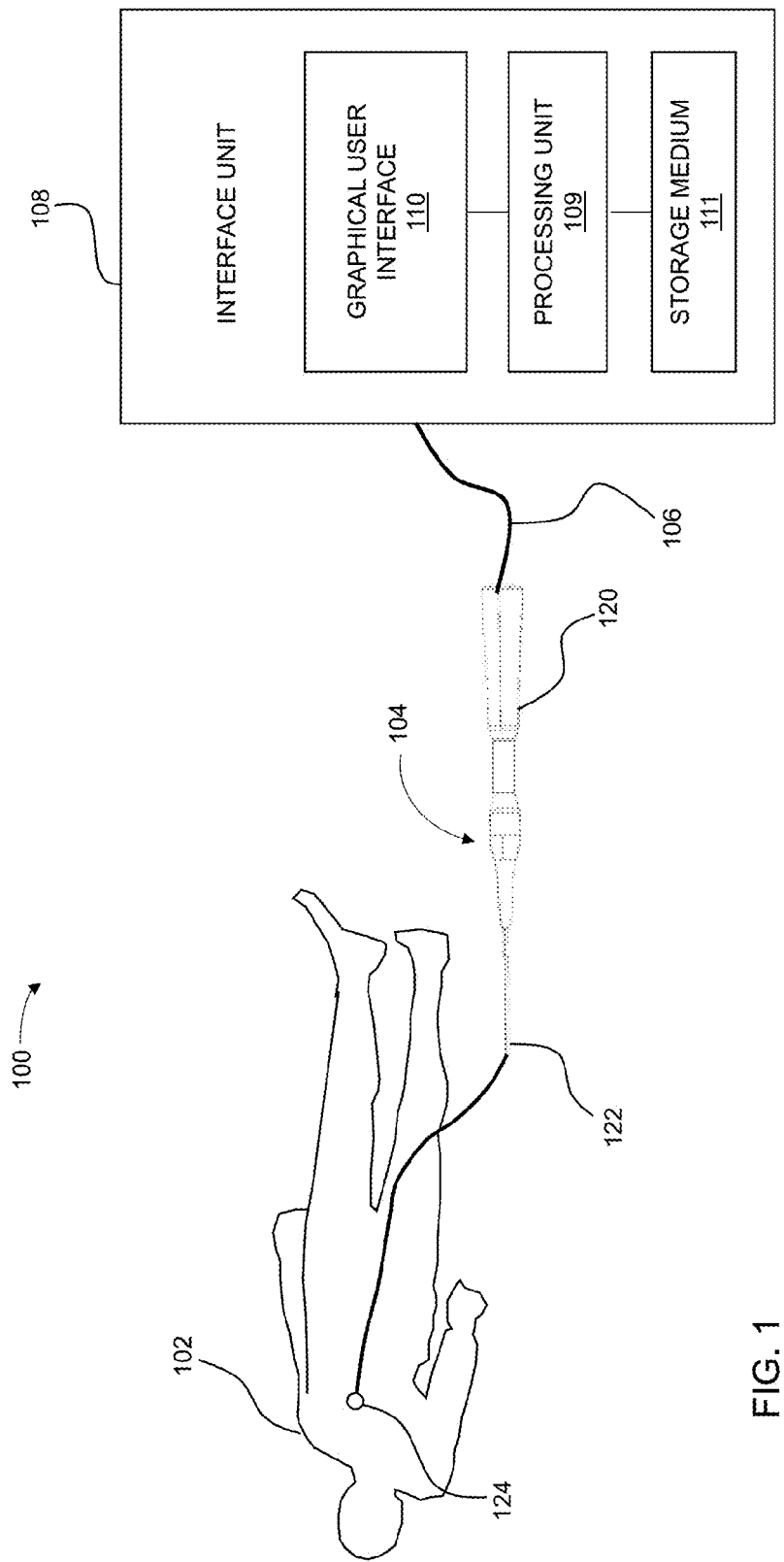
FIG. 1 is a schematic representation of a system during a medical procedure.

FIG. 1 is a schematic representation of a system 100 during a medical procedure performed in an anatomic structure of a patient 102. The system 100 can include a medical device 104 connected, via an extension cable 106, to an interface unit 108. The interface unit 108 can include a processing unit 109 (e.g., one or more processors), a graphical user interface 110, and a storage medium 111. The graphical user interface 110 and the storage medium 111 can be in electrical communication (e.g., wired communication, wireless communication, or both) with the processing unit 109.

In use, the medical device 104 can be moved within the anatomic structure (e.g., as part of a medical procedure) such that the processing unit 109 can receive a plurality of location signals of the medical device 104 in the anatomic structure. As described in greater detail below, the processing unit 109 can construct a three-dimensional surface representation of the anatomic structure based on a three-dimensional data structure representing locations, within the anatomic structure, visited by the medical device 104. To the extent the medical device 104 has not visited each location within the anatomic structure, a corresponding three-dimensional data structure can be an incomplete or uncertain data set. To account for such an incomplete or uncertain data set, it can be useful to volumetrically smooth the three-dimensional surface representation generated based on the three-dimensional data structure. As a result of such volumetric smoothing, however, certain portions of the three-dimensional surface representation may not pass close to the visited locations of the medical device 104 along some areas of the three-dimensional data structure. To account for such unintended distortions of the three-dimensional surface representation, as also described in greater detail below, the processing unit 109 can receive one or more inputs corresponding to one or more anchor portions for advantageously constraining a three-dimensional surface representation of the anatomic structure. For example, without modifying other parameters of a surface mesh, the three-dimensional surface representation can be constrained to include details of the anatomic structure that would not otherwise be represented in a three-dimensional surface representation based on catheter location alone.

In general, the three-dimensional surface representation of the anatomic structure formed using system 100 according to any one or more of the methods described herein can be shown on the graphical user interface 110, and the three-dimensional surface representation can be used to facilitate performance of a medical procedure by a physician. For example, as described in greater detail below, the three-dimensional surface representation of the anatomic structure and the position of the medical device 110 can be shown on the graphical user interface 110 and used as a visual guidance tool (e.g., as an analog) for movement of the medical device 104 in the anatomic structure. It should be appreciated, therefore, that the details provided in the three-dimensional surface representation generated as described herein can facilitate fine movement of the medical device 104 relative to the anatomic structure. As an example, as compared to a three-dimensional surface representation based on catheter position alone, the three-dimensional surface representation generated according to any one or more of the methods described herein can more accurately represent anatomic features or landmarks that are useful for positioning the medical device 104 relative to targeted tissue. Further, or in the alternative, as compared to a three-dimensional surface representation constructed solely from interpolation or approximation between points in a data set of known positions of the medical device 104 in an anatomic structure, the three-dimensional surface representation generated according to any one or more of the methods described herein is less likely to be unintentionally distorted in areas in which there are significant spatial gaps in position data of the medical device 104.

Figure 2:
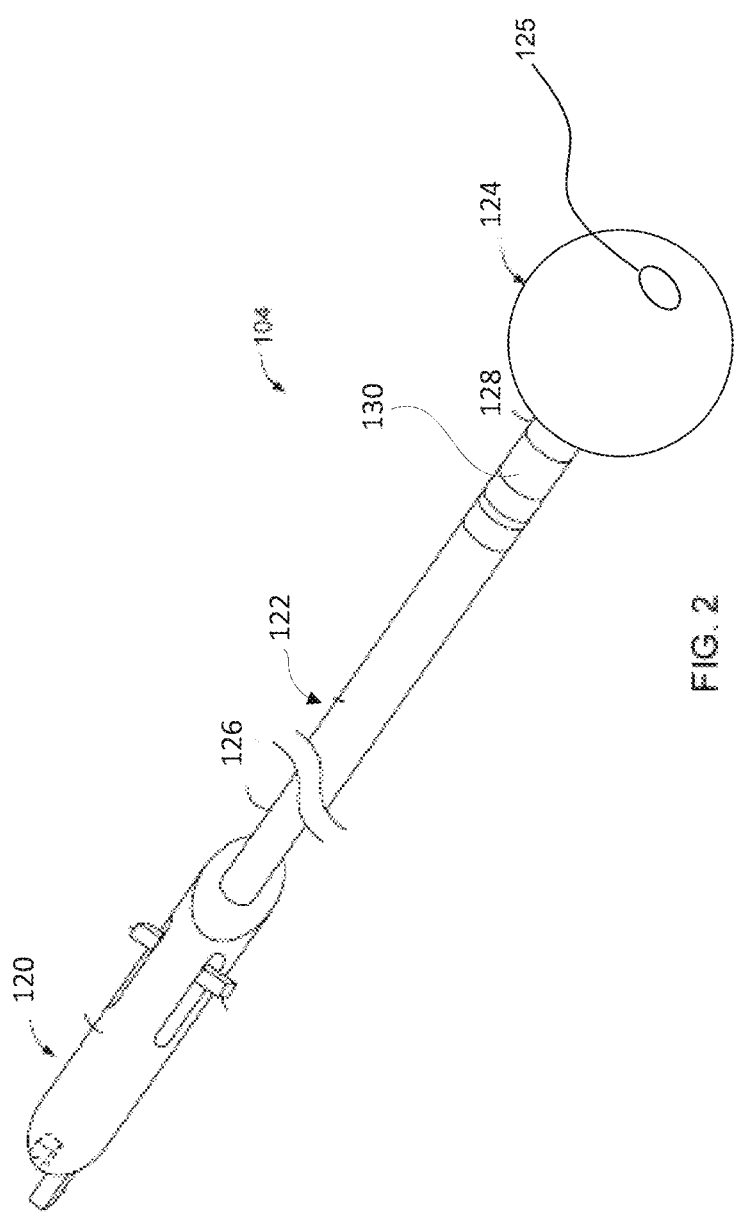
FIG. 2 is a perspective view of an exemplary medical device of the system of FIG. 1.

Referring now to FIGS. 1-2, the medical device 104 can be any of various different medical devices known in the art for use with respect to an anatomic structure and includes, therefore, any manner and form of medical devices useful for diagnosis, treatment, and combinations thereof. For the sake of explanation, and not by way of limitation, the medical device 104 is described herein as a catheter insertable into an anatomic structure. Thus, the medical device 104 can include a handle 120, a shaft 122, and a tip section 124. The shaft 122 can include a proximal portion 126 secured to the handle 120, and a distal portion 128 coupled to the tip section 124.

The tip section 124 generally includes any portion of the medical device 104 that directly or indirectly engages tissue for the purpose of treatment, diagnosis, or both and, therefore, can include any one or more of all manner and type of contact and/or non-contact interaction with tissue known in the art. For example, the tip section 124 can include one or more of contact and non-contact interaction with tissue in the form of energy interaction (e.g., electrical energy, ultrasound energy, light energy, cooling and any combinations thereof), chemical interaction with tissue, or both. Thus, for example, the tip section 124 can deliver energy (e.g., electrical energy) to tissue in the anatomic structure as part of any number of medical procedures.

In certain implementations, it is desirable to deliver energy (e.g., RF energy) from the tip section 124 to targeted portions of tissue in the anatomic structure to ablate tissue at some depth relative to a surface of the anatomic structure. In implementations in which the anatomic structure is a heart cavity, such ablations created by the tip section 124 along a surface of the anatomic structure can, for example, treat cardiac arrhythmia in patients with this condition. The effectiveness of the ablations created using the tip section 124 in such a cardiac ablation procedure, however, can be dependent upon the location of the ablations. It should be appreciated, therefore, that accurate representation of anatomic features or landmarks in the three-dimensional surface representation used to guide placement of the catheter can be advantageous for accurately delivering such targeted ablation energy to tissue in cardiac ablation procedures or other similar procedures in which there is a benefit derived from targeted energy delivery.

The medical device 104 can include a sensor 125 disposed, for example, along the tip section 124 and in electrical communication with the interface unit 108 (e.g., in communication with the processing unit 109). The sensor 125 can be any of various different types of sensors suitable for sensing contact with tissue of an anatomic structure and, therefore, can be useful for providing feedback to the interface unit 108 regarding the location of a blood-tissue boundary. In general, it should be understood that any one or more forms of feedback provided by the sensor 125 can form the basis for generating anchor portions for constraining a three-dimensional surface representation of the anatomic structure. Examples of these forms of feedback provided by the sensor 125 and useful as the basis for generating anchor portions are described below. While the sensor 125 is described herein as a single sensor for the sake of clarity of explanation, the sensor 125 can include an array of any one or more of the sensors described herein, including, for example, any combination of the sensors described herein.

As an example, the sensor 125 can include a sensing electrode such that changes to an electrical signal measured between the sensor 125 and another electrode (e.g., another sensor carried on the tip section 124) can be detected as an indication of the presence of viable tissue in contact with the sensor 125. As used herein, viable tissue is tissue that conducts an electrical signal and, thus, includes tissue that has not yet been ablated (e.g., is not scar tissue) as well as tissue that is not otherwise diseased such that conduction of the electrical signal is impaired. The detection of viable tissue in contact with the sensor 125 can include observation of the electrical signal by the physician. Also, or in the alternative, the detection of viable tissue in contact with the sensor can be based on a comparison of the electrical signal relative to a predetermined threshold (e.g., for a bipolar electrogram, a threshold of above about 0.1 mV). More generally, any of the various different devices, systems, and methods described herein can be advantageously used in combination with detecting changes to an electrical signal measured between the sensor 125 and another electrode to detect or confirm contact with tissue.

Additionally, or alternatively, the sensor 125 can include a force sensor to detect a magnitude and, optionally or additionally, a direction of force exerted on the sensor 125 through contact with a surface of the anatomic structure. Such a force sensor can include any of various different force sensors responsive to contact between the sensor 125 and tissue of the anatomic structure. Such responsiveness can be independent, or at least substantially independent, of whether or not the contacted tissue is viable. Thus, for example, the sensor 125 can be a force sensor including optical fibers, transmitting or sensing coils, and the like, for sensing force. Contact between the sensor 125 and tissue of the anatomic structure can result in an increase in measured force. For example, a contact force greater than 5 g (e.g. greater than 10 g) can be indicative of contact between the sensor 125 and tissue. The measured force can, in addition or in the alternative, be related to the degree of contact between the sensor 125 and the tissue of the anatomic structure. Additionally, or alternatively, contact between the sensor 125 and tissue of the anatomic structure can result in a measured force in a direction normal to the tissue at a point of contact.

As an additional or alternative example, the sensor 125 can include an ultrasound sensor such that the sensor 125 can detect features of an anatomic structure based on any of various different ultrasound techniques that are known in the art. As a specific example, the sensor 125 can include an ultrasound transducer such that ultrasound reflections can be measured with respect to distance along an axis of the sensor 125. Continuing with this example, contact or proximity between the sensor 125 and tissue in the anatomic structure can result in ultrasound reflections at distances corresponding a distance between the sensor 125 and the tissue.

As yet another additional or alternative example, the sensor 125 can include a deformation sensor to detect deformation (e.g., magnitude, direction, or both) of the tip section 124 as a result of contact between the tip section 124 and a surface of the anatomic structure. For example, the measured deformation can be a substantially monotonic function of the degree of contact between the sensor 125 and the tissue of the anatomic structure. Additionally, or alternatively, contact between the sensor 125 and tissue of the anatomic structure can result in deformation primarily in a direction normal to the tissue at the point of contact.

As yet another additional or alternative example, the sensor 125 can include an impedance sensor to detect a change in an electrical impedance as a result of contact between the tip section 124 and tissue of the anatomic structure. For example, in some implementations, contact between the sensor 125 and tissue in the anatomic structure can be detected as an increase in a measured impedance. Continuing with this example, an increase in a measured impedance larger than the expected variation in the impedance when the sensor 125 is not in contact with tissue (e.g. an increase greater than 100 ohms) can be indicative of contact between the sensor 125 and tissue in the anatomic structure. Additionally, or alternatively, the measured impedance can be a substantially monotonic function of the degree of contact between the sensor 125 and the tissue.

In addition to, or instead of, feedback provided by the sensor 125, contact between the tip section 124 and tissue of the anatomic structure can be based on one or more imaging modalities. The use of one such imaging modality can include observation of one or both of the tip section 124 and the shaft 122 by the physician using fluoroscopy. An additional, or alternative, modality can include observation of one or both of the tip section 124 and the shaft by the physician using intracardiac ultrasound in implementations in which the anatomic structure is a heart cavity. In some instances, based on information determined according to any one or more imaging modality, the physician can tag the location of contact with tissue, and the tag can form a basis of the one or more anchor portions near which the three-dimensional surface representation is constrained to pass. Additionally, or alternatively, information determined automatically from an image can provide an indication of contact between the tip section 124 and tissue of the anatomic structure.

While contact with tissue that forms a basis for the anchor portions can be based on feedback provided by sensors 125, it should be appreciated that anchor portions can be additionally, or alternatively, based on other types of feedback. For example, anchor portions can be placed (e.g., through tags applied by the physician) in locations in which a physician detects a resistance to movement (e.g., rotation, articulation, advancement, or a combination thereof), with resistance being indicative of contact between the medical device 104 and the tissue.

The medical device 104 can further, or instead, include a magnetic position sensor 130 along the distal portion 128 of the shaft 122. It should be appreciated that the magnetic position sensor 130 can be any of various magnetic position sensors well known in the art and can be positioned at any point along the distal portion 128. The magnetic position sensor 130 can, for example, include one or more coils that detect signals emanating from magnetic field generators. One or more coils for determining position with five or six degrees of freedom can be used.

The magnetic field detected by the magnetic position sensor 130 can be used to determine the position of the distal portion 128 of the catheter shaft 122 according to one or more methods commonly known in the art such as, for example, methods based on using a sensor, such as the magnetic position sensor 130, to sense magnetic fields indicative of the position of the magnetic position sensor 130 and using a look-up table to determine location of the magnetic position sensor 130. Accordingly, because the tip section 124 is coupled to the distal portion 128 of the shaft 122 in a known, fixed relationship to the magnetic position sensor 130, the magnetic position sensor 130 also provides the location of the tip section 124. While the location of the tip section 124 is described as being determined based on magnetic position sensing, other position sensing methods can additionally or alternatively be used. For example, the location of the tip section 124 can be additionally, or alternatively, based on impedance, ultrasound, and/or imaging (e.g., real time MRI or fluoroscopy).

Referring now to FIGS. 1-4, the tip section 124 of the medical device 104 can be moved in an anatomic structure 132 (e.g., prior to application of an ablation treatment or other type of treatment). If the tip section 124 of the medical device 104 is movable in blood in the anatomic structure 132 and obstructed only by a surface 133 of the anatomic cavity 132, the known positions of the tip section 124 of the medical device 104 can be taken together to provide an indication of the size and shape of a volume defined by the surface 133 of the anatomic structure 132 and can form a basis for a three-dimensional data structure 134 corresponding to a volume defined by the anatomic structure 132. The three-dimensional data structure 134 can include any of various different data structures known in the art. As an example, the three-dimensional data structure 134 can include an occupancy grid. As another example, the three-dimensional data structure 134 can include an indicator function. Additionally, or alternatively, the three-dimensional data structure 134 can include a segmentation mask. Further, or instead, the three-dimensional data structure 134 can include space carving.

Because it is often difficult or impractical to pass the tip section 124 through each portion of the volume defined by the surface 133 of the anatomic structure 132, the three-dimensional data structure 134 may be an incomplete or uncertain data set. As described in greater detail below, forming the three-dimensional data structure 134 based on such an incomplete or uncertain data set can have implications for accurately representing anatomic features of the surface 133 of the anatomic structure 132. For example, the three-dimensional data structure 134 can include a probabilistic model as a function of location, and an incomplete or uncertain data set of locations can result in regions of high uncertainty in the probabilistic model. Also, or instead, the three-dimensional data structure 134 can include a model with two or more discrete states (e.g., a "blood" state, an "unknown" state, a "tissue" state, a "boundary" state, and combinations thereof) as a function of location, and an incomplete or uncertain data set of locations can result in uncertain states (e.g. "unknown" states).

While the three-dimensional data structure 134 can be based on known positions of the tip section 124 of the medical device 104 in the anatomic structure 132, it should be appreciated that other methods of determining the three-dimensional data structure 134 are additionally or alternatively possible. For example, the three-dimensional data structure 134 can be based on images of the surface 133 of the anatomic structure 132 acquired prior to or during the medical procedure, particularly in use cases in which the images of the surface 133 of the anatomic structure 132 may not be complete. Such images can correspond to any of various, different imaging modalities including, for example, x-ray.

The three-dimensional data structure 134 can include, for example, a three-dimensional grid of voxels 135. In general, it should be appreciated that the three-dimensional grid of voxels 135 can be any one or more of various different types three-dimensional grids well known in the art. By way of example, the three-dimensional grid of voxels 135 can include one or more of an occupancy grid and an occupancy field. By way of further, non-exclusive example, the three-dimensional grid of voxels 135 can include a volumetric grid representation.

Each voxel 135 can be a discrete element of volume. Together, the voxels 135 can form the three-dimensional data structure 134 which, in general, is a three-dimensional notational space. As described in greater detail below, a three-dimensional surface representation 136 can be formed in relation to the three-dimensional data structure 134 such that the three-dimensional surface representation 136 can represent the surface 133 of the anatomic structure 132. In general, the three-dimensional surface representation 136 can be any one or more of the various different types well-known in the art and, thus, by way of non-exclusive example can include any one or more of the following: a "level set"; a "separating surface"; and an "implicit surface".

In certain medical procedures, it can be impractical (e.g., due to time constraints) or impossible (e.g., due to shape) to visit each location of the anatomic structure 132 with the tip section 124. Accordingly, the three-dimensional data structure 134 and/or the three-dimensional surface representation 136 can be necessarily based on certain inferences between data points. These inferences, while serving as a useful expedient for generation of the three-dimensional surface representation 136, can result in discrepancies between the three-dimensional surface representation 136 and the surface 133 of the anatomic structure 132 upon which the three-dimensional surface representation 136 is based. Such discrepancies can, for example, result in one or more anatomic features of the surface 133 of the anatomic structure 132 being obscured, or at least distorted, in the resulting three-dimensional surface representation 136.

The inferences used to form the three-dimensional surface representation 136 can include any manner and form of volumetric smoothing known in the art. For example, volumetric smoothing the three-dimensional surface representation 136 can be based on surface tension methods. As an additional or alternative example, volumetric smoothing the three-dimensional surface representation 136 can be based on hole filling methods. As a further or alternative example, volumetric smoothing the three-dimensional surface representation 136 can be based on interpolation. As still a further or alternative example, volumetric smoothing of the three-dimensional surface representation 136 can be based on ball-pivoting.

In general, discrepancies between the three-dimensional surface representation 136 and the surface 133 of the anatomic structure 132 can arise as a result of a trade-off between the degree of volumetric smoothing used to form the three-dimensional surface representation 136 and incompleteness or uncertainty of the data set forming the three-dimensional data structure 134. That is, it can be desirable to specify a low degree of volumetric smoothing to achieve resolution of certain anatomic features in the three-dimensional surface representation 136. Such resolution in one area, however, can have the unintended consequence of creating distortions in areas in which the data set is incomplete or uncertain, with such incompleteness or uncertainty being common in implementations in which the data set is based on locations in the anatomic structure 132 visited by the tip section 124. For example, the three-dimensional surface representation 136 can appear to include numerous distortions (e.g., undulations or, more specifically, invaginations) that are not representative of the surface 133 of the anatomic structure 132 when a low degree of volumetric smoothing is applied to an incomplete or uncertain data set. However, increasing the amount of volumetric smoothing of the three-dimensional surface representation 136 to remove such distortions resulting from incompleteness or uncertainty of the data set can have the unintended consequence of obscuring or distorting certain anatomic features.

Figure 3:
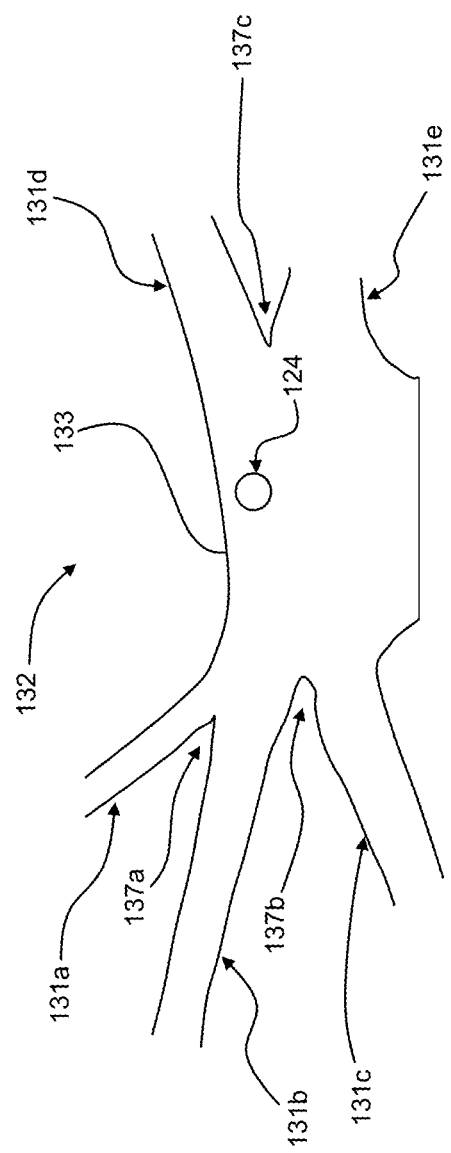
FIG. 3 is a schematic representation of a tip section of the medical device of FIG. 2 shown in an anatomic structure.
Figure 5C:
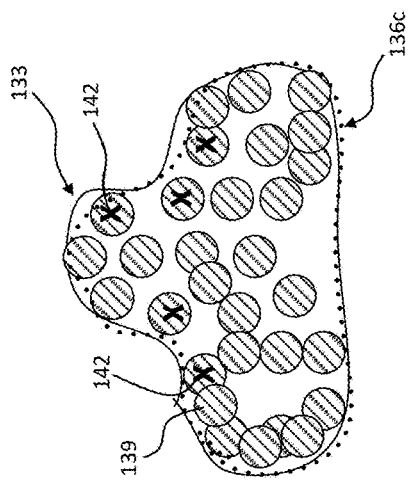
FIG. 5C is a schematic representation of a surface of the anatomic structure having superimposed thereon the point cloud of FIG. 5A and a three-dimensional surface representation constrained relative to one or more anchor portions.
Figure 5B:
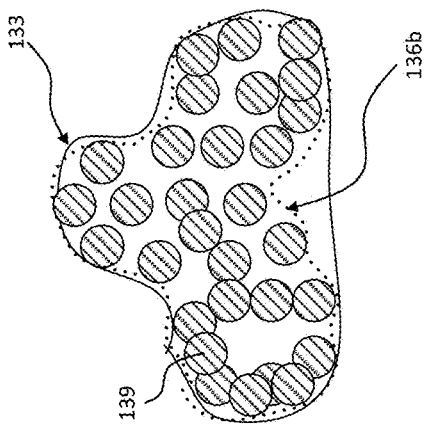
FIG. 5B is a schematic representation of a surface of the anatomic structure having superimposed thereon the point cloud of FIG. 5A and a three-dimensional surface representation with a low degree of volumetric smoothing.
Figure 5A:
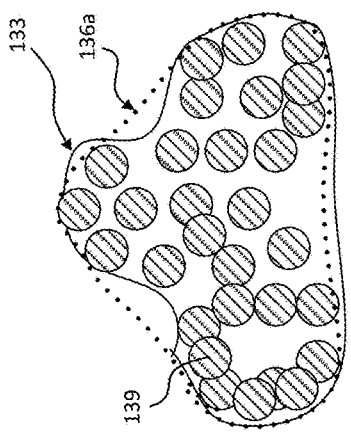
FIG. 5A is a schematic representation of a surface of the anatomic structure having superimposed thereon a point cloud, corresponding to known locations of a medical device in an anatomic structure, and a volumetrically smoothed three-dimensional surface representation with a high degree of volumetric smoothing.

FIGS. 5A-5C are, collectively, a schematic depiction of a generalized example of distortions that can occur as a result of volumetric smoothing a three-dimensional surface representation based solely on surface tension, hole filling, interpolation, ball pivoting, or other similar implicit or explicit surface reconstruction methods applied to an incomplete or uncertain data set. In each of FIGS. 5A-5C, a point cloud 139 is shown superimposed on the surface 133 of the anatomic structure 132 (FIG. 3). The point cloud 139 can correspond to, for example, known locations of the tip section 124 of the medical device 104 in the anatomic structure 132 (FIG. 3). As used, herein, the point cloud 139 should be understood to include any of various different point clouds well known in the art of surface reconstruction. In general, it is desirable to generate a volumetrically smoothed surface mesh from the point cloud 139 to create a three-dimensional surface representation that accurately represents the surface 133 of the anatomic structure 132 (FIG. 3). However, as described in greater detail below, distortions can occur when the point cloud 139 is an incomplete or uncertain data set of an anatomic structure and it is, nevertheless, desirable to represent accurately a geometric feature of the surface 133.

FIG. 5A is a schematic representation of a three-dimensional surface representation 136a of the point cloud 139, with the three-dimensional surface representation 136a volumetrically smoothed to a high degree. As shown in FIG. 5A, a high degree of volumetric smoothing of the three-dimensional surface representation 136a can result in significant deviations between the three-dimensional surface representation 136a and the surface 133 (i.e., the intended shape). For example, with a high degree of volumetric smoothing, the three-dimensional surface representation 136a can be based on an interpolation between data points of the point cloud 139 that are not close to one another, and details of the shape between the data points may be lost.

FIG. 5B is a schematic representation of a three-dimensional surface representation 136b of the point cloud 139, with the three-dimensional surface representation 136b smoothed to a low degree of volumetric smoothing. Accordingly, the three-dimensional surface representation 136b is based on interpolation between data points of the point cloud 139 that are close to one another, as compared to the interpolation associated with FIG. 5A. As shown in FIG. 5B, the interpolation between data points in the point cloud 139 that are relatively close to one another can result in a shape that shows features that are not actually present on the surface 133.

In general, it should be appreciated that inaccuracies, such as those shown in FIG. 5A and FIG. 5B, can be particularly prevalent in areas in which the surface 133 is represented by relatively few data points of the point cloud 139. However, it is often impractical or impossible to obtain a complete data set upon which the three-dimensional surface representation 136a or 136b can be based. For example, the time associated with obtaining such a complete data set may be impermissibly long. As described in greater detail below, a useful solution to this trade-off between accuracy and challenges associated with data acquisition is to constrain volumetric smoothing in areas in which the shape of the surface 133 is known or known with some level of confidence.

Referring now to FIG. 5C, one or more anchor portions 142 can be added to the data set to identify one or more known positions on the surface 133. As described in greater detail below, the one or more anchor portions 142 can constrain the volumetric smoothing of the three-dimensional surface representation 136c. Because the three-dimensional surface representation 136c is constrained relative to the one or more anchor portions 142, distortions or other types of inaccuracies associated with a high degree of volumetric smoothing (FIG. 5A) and a low degree of volumetric smoothing (FIG. 5B) are less prevalent in the three-dimensional surface representation 136c (FIG. 5C). More generally, the three-dimensional surface representation 136c is a more accurate representation of the surface 133 than would be obtained without some form of constraint relative to the one or more anchor portions 142, which represent corresponding positions known, optionally with some degree of confidence, to lie on the surface 133.

Referring again to FIGS. 1-4, the inaccuracies in the three-dimensional surface representation 136 that can result from volumetric smoothing can be particularly prevalent in locally concave areas of the surface 133 along a generally convex portion of the surface 133 of the anatomic structure 132. According to the convention used herein, the concavity of the surface 133 of the anatomic structure 132 is expressed with respect to the shape of a blood-tissue boundary formed by the surface 133 of the anatomic structure 132 (FIG. 3) around the blood. For example, as shown in FIG. 3, the anatomic structure 132 can include carina 137a, 137b, 137c between anatomic elements 131a, 131b, 131c, 131d, 131e of the anatomic structure 132. The surface 133 should be understood to be locally concave along each carina 137a, 137b, 137c. In such instances, volumetric smoothing the three-dimensional surface representation 136 can result in an inaccurate depiction of the surface 133 of the anatomic structure 132 in the region of the carina 137a, 137b, 137c. Such an inaccurate depiction in the three-dimensional surface representation 136 in the vicinity of one or more of the carina 137a, 137b, 137c can be problematic, for example, in instances in which it may be desirable to apply lesions, and thus position accurately the tip section 124, in the vicinity of one or more of the carina 137a, 137b, 137c. For example, in FIG. 3, in instances in which the anatomic structure 132 is the left atrium, it may be desirable to apply lesions in the carina 137c between the left superior pulmonary vein (LSPV) and the left inferior pulmonary vein (LIPV), represented as 131d and 131e, respectively. It should be appreciated that the anatomic structure 132 is depicted as the left atrium in FIG. 3 by way of example and not limitation, and, thus, it should be appreciated that the number and orientation of anatomic elements and corresponding carina (or other similar locally concavities) present in the anatomic structure 132 can depend on the type of anatomic structure.

To overcome the trade-off that can exist between global and local resolution of the three-dimensional surface representation 136 as a result of incomplete or uncertain data regarding the surface 133 of the anatomic structure 132, the present disclosure is generally directed to constraining the three-dimensional surface representation 136 according to one or more of the methods described herein. For example, constraining the three-dimensional surface representation 136 as described herein can facilitate accurate representation of anatomic features of the surface 133 of the anatomic structure 132 while allowing the three-dimensional surface representation 136 to be generated efficiently (e.g., based on an incomplete or uncertain data set of locations in the anatomic structure 132).

The three-dimensional data structure 134 and the three-dimensional surface representation 136 can be stored on the storage medium 111, along with instructions executable by the processing unit 109 to display the three-dimensional data structure 134, the three-dimensional surface representation 136, or both on the graphical user interface 110, as described in greater detail below. The instructions stored on the storage medium 111 and executable by the processing unit 109 to display one or both of the three-dimensional data structure 134 and the three-dimensional surface representation can be, for example, an application built using Visualization Toolkit, an open-source 3D computer graphics toolkit, available at www.vtk.org.

Figure 4:
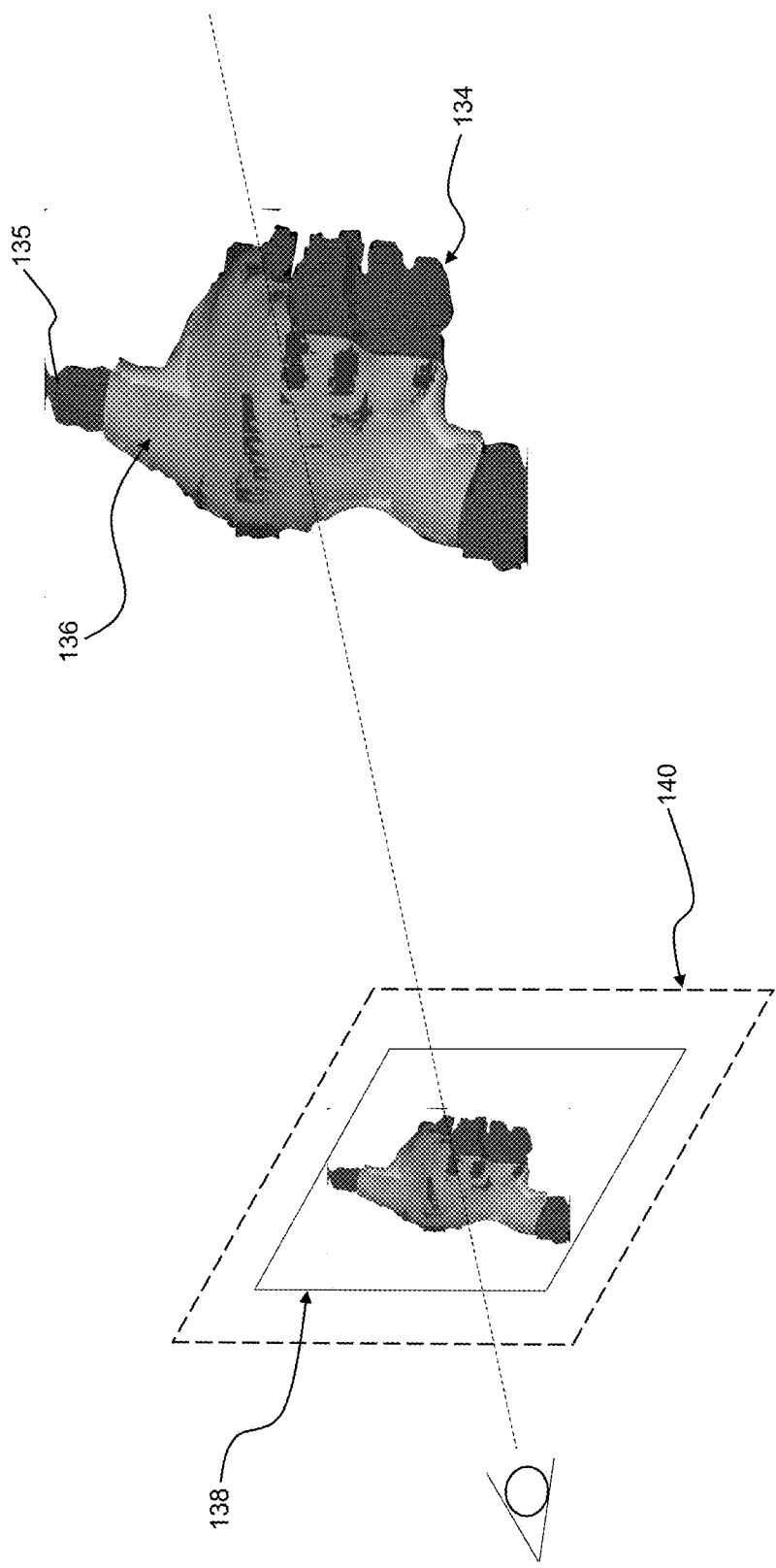
FIG. 4 is a schematic depiction of a projection of a three-dimensional data structure and a three-dimensional surface representation of the anatomic structure projected to a graphical user interface of the system of FIG. 1.

FIG. 4 is a schematic representation of the three-dimensional data structure 134 and the three-dimensional surface representation 136 projected onto a viewing window 138 of an image plane 140. While the three-dimensional data structure 134 and the three-dimensional surface representation 136 are described as both being projected onto the viewing window 138, it should be understood that the three-dimensional data structure 134 and the three-dimensional surface representation 136 can be individually projected to the viewing window 138. For example, it may be desirable to project both the three-dimensional data structure 134 and the three-dimensional surface representation 136 onto the viewing window 138 while the three-dimensional surface representation 136 is being built. Additionally, or alternatively, it may be desirable to project only the three-dimensional surface representation 136 (e.g., by making the three-dimensional data structure 134 at least partially translucent) onto the viewing window 138 while the medical device 104 (FIG. 3) is being used to diagnose and/or apply a treatment to the anatomic structure 132 (FIG. 3).

The graphical user interface 110 can be two-dimensional such that the image plane 140 corresponds to a plane of the two-dimensional display of the graphical user interface 110, and the viewing window 138 corresponds to a field of view of the two-dimensional display of the graphical user interface 110. Accordingly, the image formed by projecting one or both of the three-dimensional data structure 134 and the three-dimensional surface representation 136 onto the viewing window 138 can be displayed on the graphical user interface 110. As described in greater detail below, a physician can, in certain instances, interact with the projection of the three-dimensional data structure 134 on the graphical user interface 110 to identify one or more locations of anatomic features on the three-dimensional data structure 134 such that the three-dimensional surface representation 136, generated based on the three-dimensional data structure 134, reflects these identified anatomic features.

FIGS. 6A-6D collectively represent a sequence of images formed on the viewing window 138 and displayed on the graphical user interface 110. The sequence illustrates, in general, the generation of the three-dimensional surface representation 136.

Figure 6A:
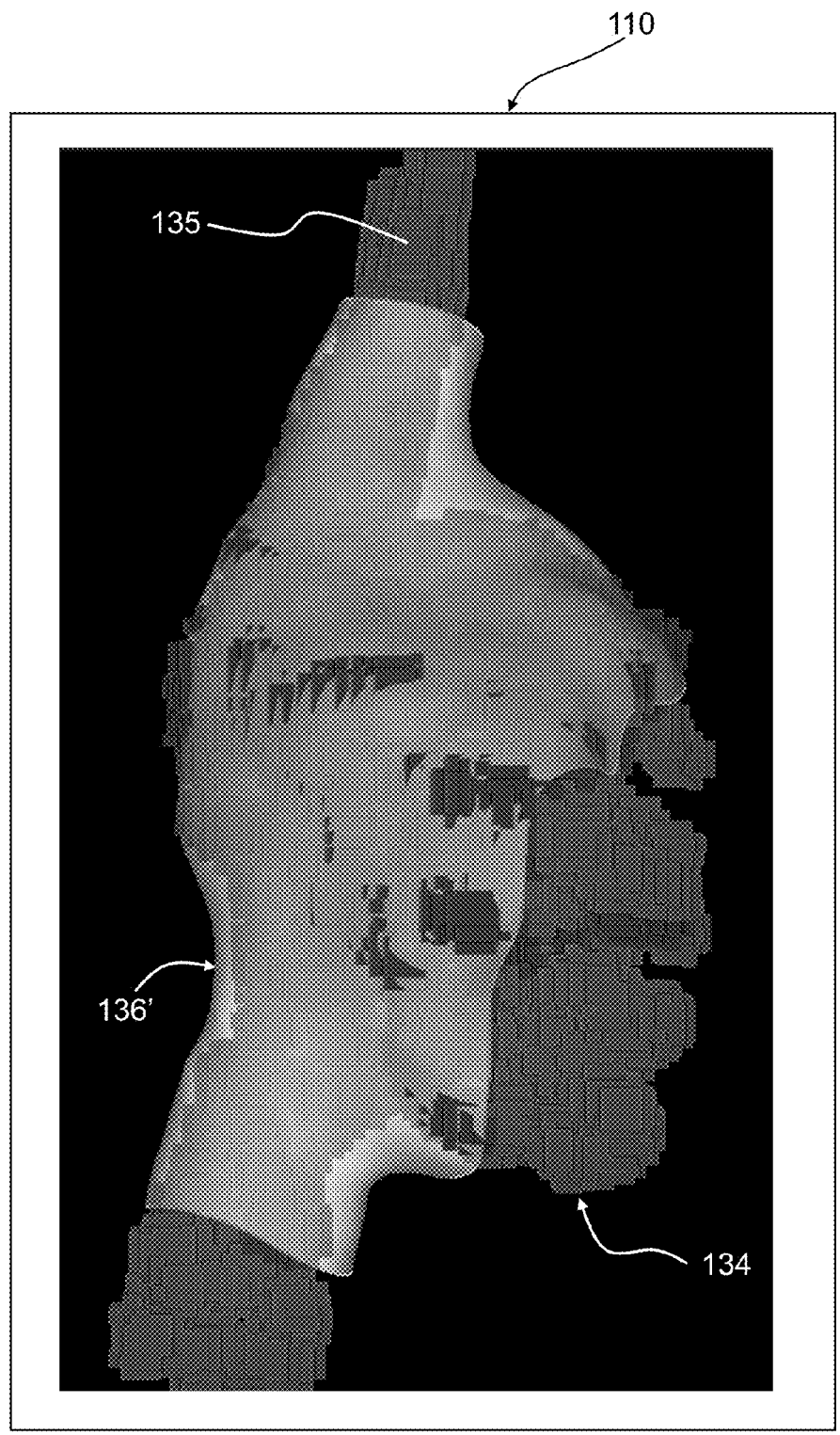
FIG. 6A is a schematic depiction of a three-dimensional data structure of FIG. 4 and an unconstrained three-dimensional surface representation displayed on the graphical user interface of the system of FIG. 1.

Referring now to FIG. 6A, the three-dimensional data structure 134 and an unconstrained three-dimensional surface representation 136' can be displayed on the graphical user interface 110. In FIG. 6A, the tricuspid valve, the inferior vena cava, and the superior vena cava have each been cut in the unconstrained three-dimensional surface representation 136' to facilitate visualization. These cuts do not constrain the surface extracted from the three-dimensional data structure 134.

The unconstrained three-dimensional surface representation 136' can represent a surface extracted from the three-dimensional data structure 134 without specific input regarding the position of anatomic features in the three-dimensional data structure 134. Thus, in certain instances, anatomic features of the surface 133 of the anatomic structure 132 (FIG. 3) may be obscured, distorted, or otherwise misrepresented in the unconstrained three-dimensional surface representation 136'. For example, the unconstrained three-dimensional surface representation 136' may not accurately represent anatomic features of the surface 133 of the anatomic structure 132 (FIG. 3) if the three-dimensional data structure 134 is based on an incomplete or uncertain data set. That is, attempts to form a surface mesh based on the three-dimensional data structure 134 can result in an obscured and/or distorted representation of the surface 133 of the anatomic structure 132 (FIG. 3), particularly along locally concave portions of the surface 133 of the anatomic structure 132 (FIG. 3).

The volumetric smoothing required to create the three-dimensional surface representation 136' based on an incomplete or uncertain data set can obscure or distort areas that are concave because the difference between missing data and an actual concave region is often not discernible by a smoothing algorithm, such as a surface tension algorithm, a hole filling algorithm, an interpolation algorithm, a ball-pivoting algorithm, or other similar algorithms. As a result, volumetric smoothing required to form the three-dimensional surface representation 136' based on an incomplete or uncertain data set can have the unintended consequence of covering over concave regions. Conversely, while it may be possible to capture aspects of local detail by decreasing the degree of volumetric smoothing used to form the three-dimensional surface representation 136', a low degree of volumetric smoothing can create distortions along other portions of the three-dimensional surface representation 136', such as where the data set is incomplete or uncertain. Accordingly, while the degree of volumetric smoothing can be adjusted to capture aspects of local detail, such adjustments can have a negative impact on the accuracy of the overall shape of the three-dimensional surface representation 136'.

Figure 6B:
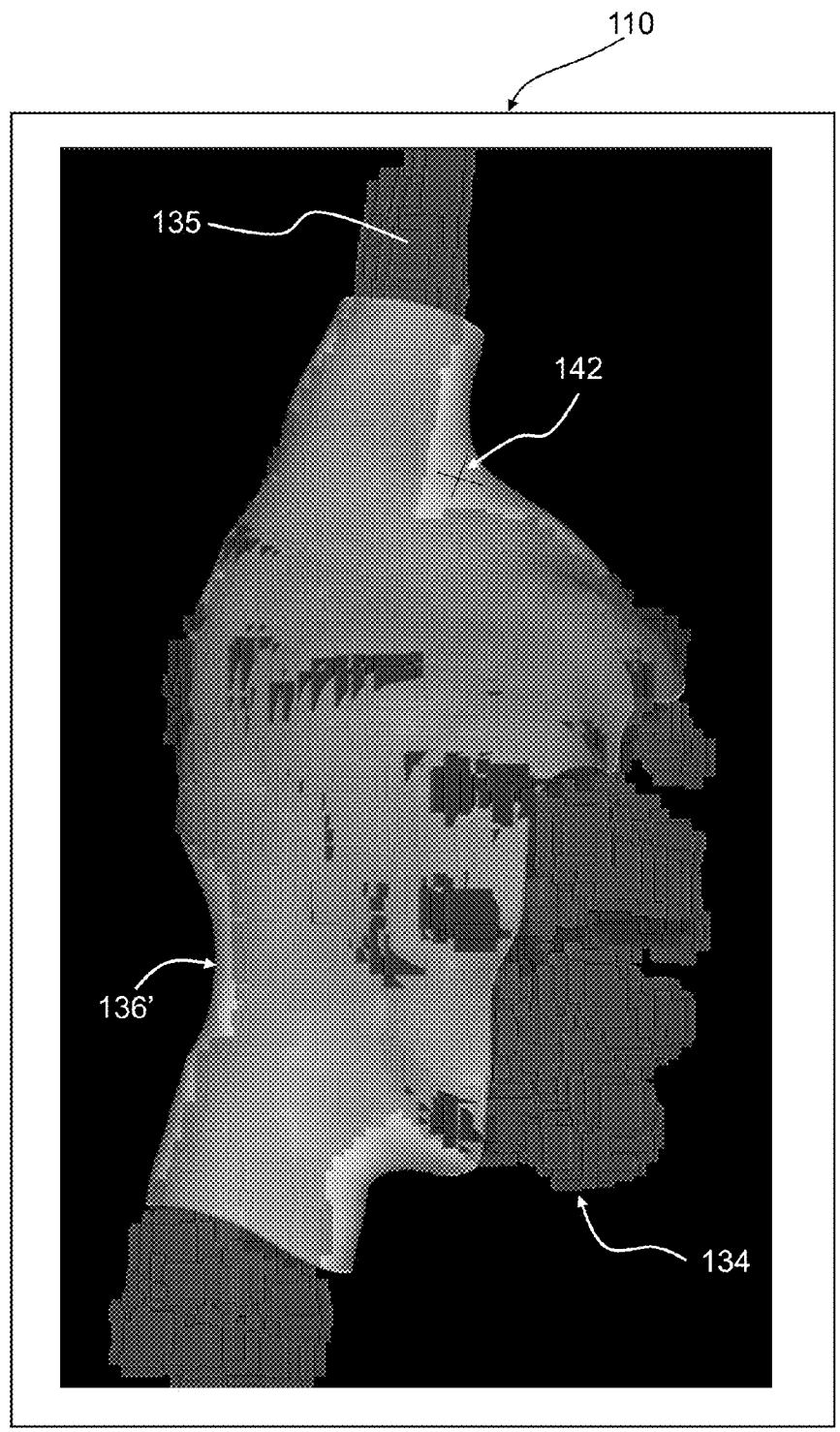
FIG. 6B is a schematic depiction of the three-dimensional data structure and the unconstrained three-dimensional surface representation of FIG. 6A displayed on the graphical user interface of the system of FIG. 1 with an anchor portion identified on the three-dimensional data structure.

Referring now to FIGS. 2, 3, and FIG. 6B, an advantageous alternative to varying the degree of volumetric smoothing of the surface mesh forming the three-dimensional surface representation 136' can include receiving identification of the one or more anchor portions 142 on the three-dimensional data structure 134. Each anchor portion 142 can correspond to a predetermined number of voxels 135 of the three-dimensional data structure 134. Additionally, or alternatively, each anchor portion 142 can correspond to one or more nodes or points in the three-dimensional data structure 134. In certain implementations, each anchor portion 142 can include information regarding, for example, an orientation of the surface 133 of the anatomic structure 132. Additionally, or alternatively, each anchor portion 142 can include information regarding, for example, a degree of confidence in the location of the anchor portions 142 and/or the associated information.

Identification of each anchor portion 142 can be based on input received from a physician (e.g., as a tag), input received from the tip section 124 in the anatomic structure 132, or a combination thereof. More generally, it should be appreciated that the identification of each anchor portion 142 can be based on observations made or prior knowledge regarding the anatomic structure 132 and can be independent of parameters used to form the three-dimensional surface representation 136'.

Each anchor portion 142 can be represented on the graphical user interface 110 as visual indicia. Such visual indicia can be useful, for example, as a visualization tool for the physician to assess how the three-dimensional surface representation 136' will be modified as it is constrained to pass near a position relative to the anchor portion 142. For example, based on observation of the visual indicia representing the anchor portion 142 on the graphical user interface 110, the physician can reposition the anchor portion 142.

The one or more anchor portions 142 can represent a position of an anatomic feature of the anatomic structure 132. For example, the one or more anchor portions 142 can correspond to locations at which contact between the tip section 124 and the surface 133 of the anatomic structure 132 is detected such that the one or more anchor portions 142 represent a location known, optionally with some confidence, to lie on the surface 133 of the anatomic structure 132. In some instances, the one or more anchor portions 142 can include information regarding, for example, a direction of contact corresponding to an orientation of the surface 133 of the anatomic structure 132. Contact detection forming the basis of the one or more anchor portions 142 can be based on any of various different forms and combinations of contact detection described herein or otherwise known in the art. For example, in cardiac applications, contact detection can be based on an intracardiac electrogram indicative of contact between the sensor 125 of the tip section 124 and the surface 133. As another, non-exclusive example, contact detection can also, or instead, be based on a force signal (e.g., including magnitude, direction, or both) in implementations in which the sensor 125 is a force sensor. As yet another, non-exclusive example, contact detection can also, or instead, be based on detecting deformation (e.g., using the sensor 125) of at least a portion of the tip section 124 as the tip section 124 contacts the surface 133. As still another, non-exclusive example, contact detection can also, or instead, be based on detecting a change in impedance (e.g. using the sensor 125).

Additionally, or alternatively, the one or more anchor portions 142 can be based on input from a physician. For example, the input from the physician can be based on the unconstrained three-dimensional surface representation 136' and the physician's knowledge of anatomy. That is, the global shape of the unconstrained three-dimensional surface representation 136' may represent the overall shape of surface 133 of the anatomic structure 132, albeit with local inaccuracies with respect to some anatomic features. In such instances, the physician can provide an indication of one or more anchor portions 142 on the three-dimensional data structure 134 and/or on the unconstrained three-dimensional surface representation 136' based on the physician's knowledge of anatomy (e.g., knowledge of the position of a carina in implementations directed to a heart cavity). As another or alternative example, the physician can provide an indication of one or more anchor portions 142 on the three-dimensional data structure 134 and/or on the unconstrained three-dimensional surface representation 136' based on observation of the tip section 124 and/or the shaft 122. That is, in certain instances, the physician can push the tip section 124 gently and observe, optionally through fluoroscopy or other similar imaging modality, whether the tip section 124 (FIG. 3) advances in response to the push. If the tip section 124 (FIG. 3) does not advance in response to the push, the physician can manually tag the point as one of the one or more anchor portions 142.

The physician can identify the one or more anchor portions 142 on the three-dimensional data structure 134 by providing inputs to the interface unit 108 (FIG. 1) (e.g., through a keyboard, a mouse, or other input associated with the interface unit 108).

Figure 6C:
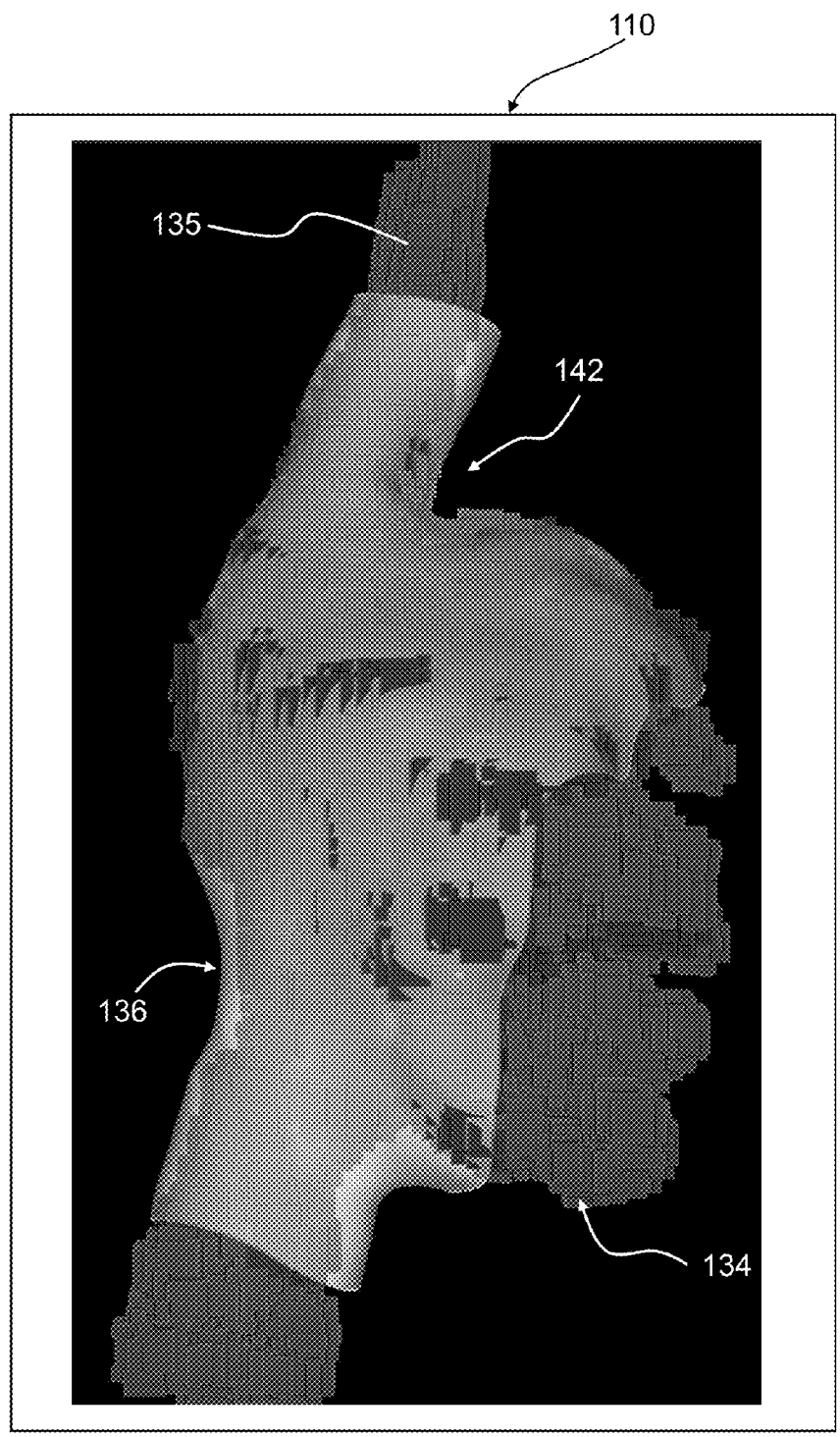
FIG. 6C is a schematic depiction of the three-dimensional data structure of FIG. 6A and a three-dimensional surface representation constrained relative to the anchor portion of FIG. 6B, the three-dimensional data structure and the three-dimensional surface representation displayed on the graphical user interface of the system of FIG. 1, with the three-dimensional surface representation surface smoothed.

Referring now to FIG. 6C, the three-dimensional surface representation 136 can be generated as a mesh (e.g., a continuous polygonal mesh) of a surface extracted from the three-dimensional data structure 134 and constrained relative to the one or more anchor portions 142. As used herein, constraining the three-dimensional surface representation 136 relative to the one or more anchor portions 142 can include any one or more of various different methods that, as compared to the absence of a constraint, reduces the distance between the three-dimensional surface representation 136 and the one or more anchor portions 142. For example, constraining the three-dimensional surface representation 136 relative to the one or more anchor portions 142 can include constraining the three-dimensional surface representation 136 to pass through the one or more anchor portions 142. Additionally, or alternatively, constraining the three-dimensional surface representation 136 relative to the one or more anchor portions 142 can include constraining the three-dimensional surface representation 136 to be at or within a distance (e.g., a fixed distance) relative to the one or more anchor portions 142. As a further or alternative example, the three-dimensional surface representation 136 can be constrained by a penalty (e.g., cost) function that penalizes for distance from the one or more anchor portions 142 but does not strictly restrict the three-dimensional surface representation 136 to pass within a specified distance of the one or more anchor portions 142.

Referring to FIGS. 6A-6C, in certain implementations, constraining the three-dimensional surface representation 136 relative to the one or more anchor portions can include setting a fixed value of one or more nodes associated with the one or more anchor portions 142 in the three-dimensional data structure 134, determining a scalar function on at least a portion of the three-dimensional data structure 134, and applying an algorithm to extract an isosurface based in part on the scalar function. An indicator function is a well-known example of such a scalar function. An embedding function is another well-known example of such a scalar function. The isosurface extracted based at least in part on the scalar function can include any of various different isosurfaces known in the art and, thus, among various examples, can include an implicit surface.

As an example, constraining the three-dimensional surface representation 136 can include a clamped signed distance function based only on space carving information, as is well known in the art. Specifically, a first fixed value can be assigned to nodes, in the three-dimensional data structure 134, corresponding to locations within the anatomic structure 132 (FIG. 3) visited by the tip section 124 of the medical device 104 (FIG. 2). Because the tip section 124 of the medical device 104 (FIG. 2) can only move through blood, the nodes with the first fixed value in the three-dimensional data structure 134 imply the presence of blood at those positions. However, because the tip section 124 of the medical device 104 (FIG. 2) does not generally move through every location within the anatomic structure 132 (FIG. 3), the nodes that have not been set to the first fixed value can correspond to one of two physical states. That is, the nodes that have not been set to the first fixed value can correspond to i) locations in the anatomic structure 132 (FIG. 3) that have not been visited by the tip section of the medical device 104 (FIG. 2) or ii) locations that are outside of the volume of the anatomic structure 132 in which the tip section 124 of the medical device 104 (FIG. 2) is moving. In general, inaccuracies in the three-dimensional surface representation 136 (such as the inaccuracies shown in FIGS. 5A and 5B) can arise from mischaracterization of these two categories of nodes that have not been set to the first fixed value.

Continuing with this example, because the one or more anchor portions 142 correspond to one or more locations on the surface 133 of the anatomic structure 132 (FIG. 3), the one or more anchor portions 142 can provide a constraint that is useful for more accurately characterizing nodes that that have not been set to the first fixed value. In some implementations, the one or more anchor portions 142 can be set to a second fixed value, different from the first fixed value. It should be appreciated that the second fixed value can be one of two values of a signed clamped distance function, and the anchor portions 142 can correspond to surfaces acquired from a range scan. In this example, therefore, nodes corresponding to the first fixed value can correspond to the known locations of blood while nodes corresponding to the second fixed value can correspond to the known locations of the surface 133 (FIG. 3) and, thus, the blood-tissue boundary. The values of the remaining nodes in the three-dimensional data structure 134 (i.e., the nodes that have been assigned neither the first fixed value nor the second fixed value) are variable.

As is known in the art, a volumetric smoothing algorithm (e.g., a three-dimensional smoothing kernel) can be applied to the three-dimensional data structure 134, and the values of these variable nodes can take on values that are a function of neighboring nodes. For example, the values of the variable nodes can take on values that are a function of neighboring nodes according to a thermal diffusion model. It should be appreciated that, because the one or more anchor portions 142 have a fixed value in this example, the one or more anchor portions 142 can modify the values of neighboring variable nodes as the three-dimensional data structure 134 undergoes volumetric smoothing. For example, a spatial convolution can be applied one or more times to calculate new values for only the variable nodes.

The three-dimensional surface representation 136 can be based on the three-dimensional data structure 134 having fixed-value nodes as described above. For example, the three-dimensional surface representation 136 can correspond to an isosurface (e.g., a level set, an implicit surface, etc.) extracted from the three-dimensional data structure 134 having fixed-value nodes. In certain implementations, a "marching cubes" algorithm can be applied to the volumetrically smoothed three-dimensional data structure 134 having fixed-value nodes to extract an isosurface corresponding to a fixed value (e.g., a value between the first fixed value associated with known locations of the tip section 124 of the medical device 104 (FIG. 2) and the second fixed value associated with the one or more anchor portions 142). In this way, the one or more anchor portions 142 can have the effect of constraining, or otherwise limiting, the position of the resulting three-dimensional surface representation 136 extracted from the three-dimensional data structure 134. Additionally, or alternatively, a "flying edges" algorithm can be applied to the volumetrically smoothed three-dimensional data structure 134 to extract an isosurface.

Further, or instead, the three-dimensional surface representation 136 can be based on any of various different algorithms well known in the art for extracting a mesh of a surface from the three-dimensional data structure 134. Thus, for example, the three-dimensional surface representation 136 can be a polygonal mesh extracted from the three-dimensional data structure 134 based on a "marching cubes"

algorithm and constrained relative to the one or more anchor points 142 according to any of the various different methods described herein. As used herein, a "marching cubes" algorithm can include any one or more algorithms in which a polygonal mesh of an isosurface is extracted from the three-dimensional data structure 134 based on analysis of node values in the three-dimensional data structure 134. More generally, the three-dimensional surface representation 136 can be extracted from the three-dimensional data structure 134 according to any one or more computational algorithms known in the art for volumetrically smoothing three-dimensional representations of objects including a "ball-pivoting" algorithm, a "power crust" algorithm, and other similar algorithms.

As an example, an adaptive ball-pivoting algorithm can constrain the three-dimensional surface representation 136 relative to the anchor portions 142. That is, away from the anchor portions 142, the ball forming the basis of the ball-pivoting algorithm can be a fixed global size that yields volumetric smoothing where specific information about anatomical features is not available. For example, the fixed global ball can have a diameter between about 10 mm and 30 mm (e.g. about 15 mm). Close to the anchor portions 142, the size of the ball can be reduced to facilitate passing the surface representation 136 closer to the anchor portions 142. For example, as compared to the fixed global size of the ball away from the anchor portions 142, the size of the ball can be reduced closer to the anchor portions 142. With such a reduced ball size, as compared to the fixed global size, the three-dimensional surface representation 136 can pass closer to the anchor portions 142. As a more specific example, the size of the ball at a surface location closest to a respective one of the anchor portions 142 can be chosen such that the three-dimensional surface representation 136 lies within a predetermined minimum distance to the respective anchor portion 142. In certain implementations, the size of the ball can vary between the reduced ball size and the global ball size as a function (e.g., a linear function) of distance from the ball to the one or more anchor portions 142 until the ball size reaches the global ball size, beyond which distance the global ball size can remain at the fixed global ball size.

As shown in FIG. 6C, the three-dimensional surface representation 136 can be volumetrically smoothed and, optionally, surface smoothed. For example, volumetric smoothing of the three-dimensional surface representation 136 can be accomplished using any one or more of various different volumetric smoothing techniques that are well known in the art and described herein. Surface smoothing can additionally, or alternatively, be accomplished using any one or more of various different surface smoothing techniques well known in the art. An example of such a surface smoothing technique is Laplacian smoothing and variations thereof. In certain instances, through surface smoothing, three-dimensional surface representation 136 may no longer satisfy the constraints previously applied as part of the volumetric smoothing process. For example, as shown in FIG. 6C, the surface-smoothed three-dimensional surface representation 136 may contain fewer than all of the locations visited by the medical device. Further, or instead, the distance between the three-dimensional surface representation 136 and the anchor portions 142 may change as the three-dimensional surface representation 136 is subjected to surface smoothing.

Comparing FIG. 6B to FIG. 6C, it should be appreciated that the three-dimensional surface representation 136 differs from the unconstrained three-dimensional surface representation 136' near the one or more anchor portions 142. In particular, because the three-dimensional surface representation 136 is constrained relative to the one or more anchor portions 142, the three-dimensional surface representation 136 depicts anatomic features that are not readily apparent in the unconstrained three-dimensional surface representation 136'. Accordingly, it should be further appreciated that the one or more anchor portions 142 can facilitate efficiently generating an accurate representation of anatomic features of the anatomic structure 132 (FIG. 3).

Figure 6D:
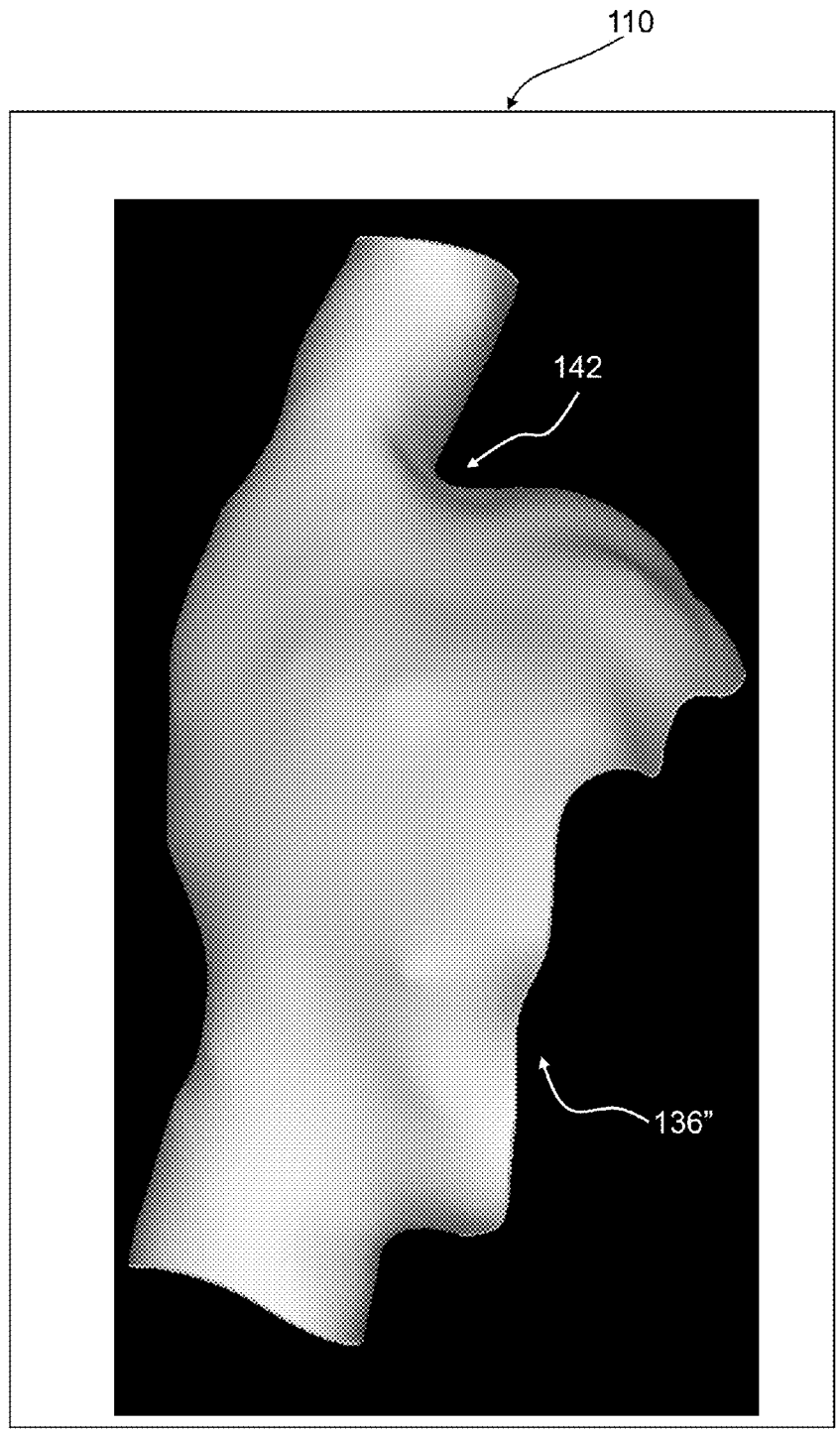
FIG. 6D is a schematic depiction of the three-dimensional surface representation of FIG. 6C displayed on the graphical user interface of the system of FIG. 1.

Referring now to FIG. 6D, the display of the three-dimensional data structure 134 of FIG. 6C can be hidden (e.g., made translucent) such that the three-dimensional surface representation 136 can be displayed by itself. The display of the three-dimensional surface representation 136 by itself and, optionally, in smoothed form can be useful, for example, for facilitating perception by the physician.

The steps shown in FIGS. 6A-6D have been shown and described as occurring in sequence for the sake of clarity of explanation. It should be appreciated, however, that in addition to, or as an alternative, any one or more of the steps shown in FIGS. 6A-6D can be combined, performed in parallel, and/or varied in order.

The computer executable instructions stored on the storage medium 111 (FIG. 1) can cause the processing unit 109 (FIG. 1) to generate the three-dimensional surface representation 136 according to one or more of the following exemplary methods. Unless otherwise indicated or made clear from the context, each of the following exemplary methods can be implemented using the system 100 (FIG. 1) and/or one or more components thereof.

Figure 7:
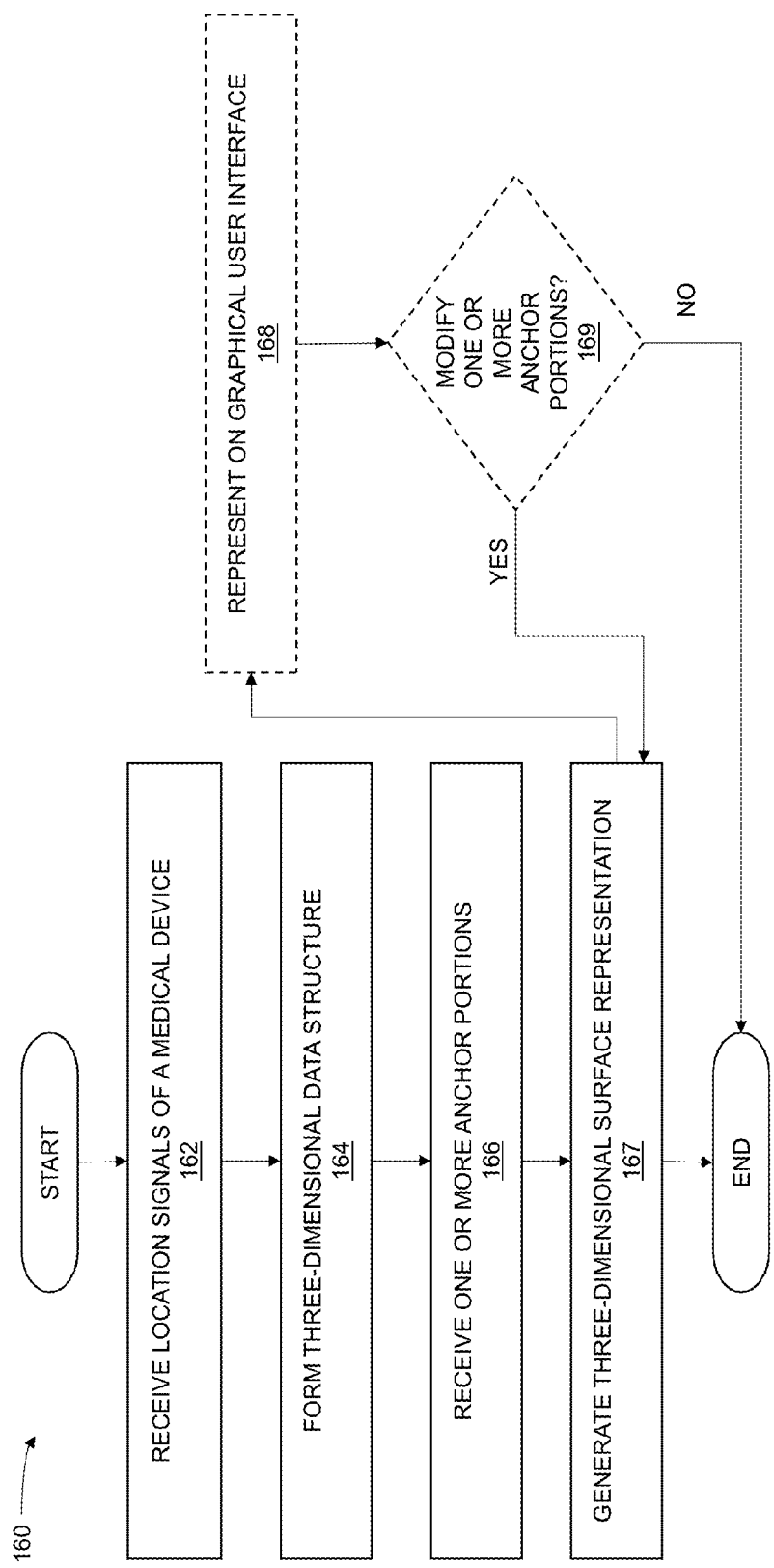
FIG. 7 is a flowchart of an exemplary method of representing a surface of an anatomic structure.

FIG. 7 is a flowchart of an exemplary method 160 of representing a surface of an anatomic structure. The exemplary method 160 can include receiving 162 a plurality of location signals of a medical device, forming 164 a three-dimensional data structure representing volumes, within the anatomic structure, occupied by the medical device at the locations corresponding to the plurality of location signals, receiving 166 one or more anchor portions representing locations relative to the anatomic structure, and generating 167 a three-dimensional surface representation of the anatomic structure. The generated 167 three-dimensional surface representation can be constrained relative to the one or more anchor portions and to contain at least a portion of the three-dimensional data structure. That is, in general, the one or more anchor portions can modify the behavior of an algorithm in a way that constrains the resulting three-dimensional surface representation relative to the anchor portions.

In general, receiving 162 the plurality of location signals of the medical device can include receiving one or more signals indicative of the location of the medical device according to any one or more of the methods described herein. The received 162 plurality of location signals can be, for example, a plurality of signals received from a single sensor over a period of time. For example, the received 162 plurality of location signals can be one or more signals from a magnetic position sensor (such as the magnetic position sensor 130 described above with respect to FIG. 2). Additionally, or alternatively, the received 162 plurality of location signals can be a plurality of signals received from multiple, different types of sensors that individually, or in combination, provide information regarding the location of the medical device in the anatomic structure. As an example, greater details of which are described below, receiving 162 the plurality of location signals of the medical device can include receiving one or more signals from a magnetic position sensor and from a sensor providing a signal indicative of a blood-tissue boundary of the anatomic structure.

As used herein, the received 162 plurality of location signals of the medical device generally correspond to locations visited by a tip section of the medical device (e.g., the tip section 124 of the medical device 104 of FIG. 2) in the anatomic structure. More generally, however, it should be understood that the plurality of location signals of the medical device can correspond to locations visited by any portion of the medical device that can be sensed or otherwise determined in the anatomic structure.

Forming 164 the three-dimensional data structure representing locations, within the anatomic structure, visited by the medical device can include forming a three-dimensional grid, with locations in the three-dimensional grid reflecting locations visited by the medical device in the anatomic structure. In such implementations, a boundary of the anatomic structure can be approximated through analysis of neighbor locations and/or node values of the three-dimensional grid such as, for example, through application of one or more of a "marching cubes" algorithm, a "ball-pivoting" algorithm, and a "power crust" algorithm, with the algorithm or algorithms extracting a surface from the three-dimensional grid. In some implementations, the one or more anchor portions (e.g., the anchor portions 142 in FIGS. 5A-5C) can be represented by respective constrained values (or combinations thereof) on the three-dimensional grid or, more generally, on any type of three-dimensional data.

In general, receiving 166 the one or more anchor portions representing locations relative to the anatomic structure can include receiving input from one or more sources. For example, receiving 166 the one or more anchor portions can be based on input received from a physician, input received from one or more sensors on the medical device, or a combination thereof. In instances in which receiving 166 the one or more anchor portions is based on a combination of input from the physician and from one or more sensors on the medical device, it can be advantageous to have a hierarchy of input such that, for example, the input from the physician can override the input from the one or more sensors on the medical device.

Receiving 166 the one or more anchor portions representing locations relative to the anatomic structure can include receiving, from one or more sensors disposed on the medical device, a signal indicative of contact between the medical device and tissue of the anatomic structure. Sensed contact (e.g., one or more of location, direction, force, consistency, and/or duration of contact) between the medical device and the surface of the anatomic structure can be indicative of a blood-tissue boundary of the anatomic structure of the patient. Accordingly, one or more anchor portions can be identified at the location of the sensed contact to ensure that the three-dimensional surface representation is constrained relative to the sensed contact, which is known to represent the blood-tissue boundary.

It should be appreciated that such a signal indicative of contact between the medical device and tissue of the anatomic chamber can include any one or more of the signals indicative of contact described herein. Thus, for example, the signal indicative of contact between the medical device and tissue of the anatomic chamber can include an impedance signal (e.g., a change in impedance) from one or more impedance sensors (e.g., the sensor 125 in FIG. 2) disposed on the medical device. Additional or alternative examples of signals indicative of contact between the medical device and the surface of the anatomic structure of the patient can include one or more of: a change in an electrical signal (e.g., electrogram or impedance) in one or more electrodes of the medical device; a force detected by a force sensor of the medical device; an ultrasound signal of an ultrasound sensor on the medical device; and a deformation of at least a portion of the medical device. As a more specific example, a signal indicative of contact between the medical device and the surface of the anatomic structure of the patient can include an amplitude derived from an electrogram detected by one or more electrodes of the medical device.

Receiving 166 the one or more anchor portions can include identification of a subset of the plurality of received location signals. Identification of the subset of the plurality of received location signals can, for example, include an input command from the physician identifying one or more portions of the three-dimensional data structure as corresponding one or more anchor portions. The input command can be received from any of various, different input devices such as a keyboard, a mouse, a touchscreen, etc. and, additionally, or alternatively, can include voice commands. Thus, in implementations in which the data structure includes a three-dimensional grid, the physician can provide input through one or more input devices to identify the subset as one or more voxels of the three-dimensional grid, as displayed on a graphical user interface.

In certain implementations, receiving 166 the one or more anchor portions can include receiving a respective confidence level associated with the one or more anchor portions. For example, a confidence level can increase substantially monotonically with a measured indication of contact (e.g. electrogram amplitude, impedance, force, deformation, and/or proximity). In such implementations, constraining the three-dimensional surface representation relative to the one or more anchor portions can be based on the respective confidence level associated with each of the one or more anchor portions. For example, the confidence levels can form a basis for certain of the one or more anchor portions acting as stronger or weaker anchor portions relative to other anchor portions. That is, an anchor portion corresponding to a higher confidence level can act as a stronger anchor as compared to an anchor portion corresponding to a weaker confidence level. Additionally, or alternatively, an anchor portion identified with contact in a known direction can constrain the normal direction of the resulting surface using any of various different techniques known in the art.

In general, generating 167 the three-dimensional surface representation of the anatomic structure can include any one or more of the methods described herein for forming a three-dimensional surface. Thus, for example, generating 167 the three-dimensional surface representation can include extracting a surface from the three-dimensional data structure according to an algorithm, such as one or more of a "marching cubes" algorithm, a "ball-pivoting" algorithm, and a "power crust" algorithm, in which the three-dimensional surface representation is constrained relative to the one or more anchor portions according to any one or more of the various different methods of constraint described herein.

Additionally, or alternatively, the three-dimensional surface representation can include a mesh (e.g., a continuous mesh). The mesh can be formed of, for example, a plurality of polygons (e.g., triangles) combined together to represent contours of the surface of the anatomic structure.

In some implementations, the generated 167 three-dimensional surface representation can be smoothed according to any of various different smoothing techniques known in the art to provide a more realistic representation of the surface of the anatomic structure.

The exemplary method 160 can optionally include representing 168, on a graphical user interface, any of various different combinations of the three-dimensional surface representation, the anchor portions, and the three-dimensional data structure. The graphical user interface can be, for example, a two-dimensional graphical user interface such as the graphical user interface 110 (FIG. 1). Accordingly, the exemplary method 160 can include representing 168, on the graphical user interface, a two-dimensional projection of the three-dimensional surface representation. In addition, or in the alternative, the exemplary method 160 can include representing 168, on the graphical user interface, a two-dimensional projection of the three-dimensional data structure.

In certain implementations, the exemplary method 160 can further include representing 168 the one or more anchor portions on the graphical user interface. For example, the one or more anchor portions can be represented 168 on the graphical user interface on a projection of the three-dimensional data structure, on a projection of the three-dimensional surface representation, or both. Additionally, or alternatively, the one or more anchor portions can be represented 168 on the graphical user interface separately from the three-dimensional data structure and/or the three-dimensional surface. It should be appreciated that representing 168 the one or more anchor portions on the graphical user interface can, for example, facilitate modification of the one or more anchor portions in certain instances. Additionally, or alternatively, the one or more anchor portions can be represented 168, on the graphical user interface, as annotations on the three-dimensional surface representation of the anatomic structure. The annotations can include, for example, tags of corresponding anatomic features, tags corresponding to locations for application of treatment (e.g., ablation), or combinations thereof. By way of example, the annotations can constrain the three-dimensional surface representation to remain unchanged as other anchor portions are added. As a further or alternative example, the three-dimensional surface representation can be constrained to pass through a portion of the three-dimensional data structure nearest to the annotation.

In certain implementations, the exemplary method 160 can optionally include determining 169 whether the one or more anchor portions have been modified. If the one or more anchor portions are determined 169 to be modified, the generating step 167 can be repeated. Thus, in general, the exemplary method 160 can be iterative. That is, in response to the generated 167 three-dimensional surface representation, the physician can continue to make modifications as necessary. These modifications can be based on one or more inputs received from any one or more of various input devices known in the art and described herein. Accordingly, modifying the one or more anchor portions can be based on one or more inputs from a keyboard, a mouse, a touchscreen, the medical device, or combinations thereof.

Modifying the one or more anchor portions can include removing at least one of the one or more anchor portions. Such removal can be useful, in certain instances, for adjusting the three-dimensional surface representation (e.g., after the three-dimensional surface representation has been generated 167) to achieve a shape that is more accurate. Additionally, or alternatively, removal of at least one of the one or more anchor portions can correct an incorrectly identified anchor portion. It should be appreciated, therefore, that removal of at least one of the one or more anchor portions can serve as an "undo" function such that correction of an incorrectly identified anchor portion does not require the physician to engage, for example, in a complex editing process. More generally, modifying the identified one or more anchor portions and repeating the generating step 167 as part of the iterative process described herein can facilitate efficient and accurate generation of the three-dimensional surface representation of the anatomic structure, as compared to tools that allow a user to selectively delete subvolumes. That is, selecting a subvolume on a two-dimensional graphical user interface commonly requires multiple selection steps from different views, which can be time consuming and subject to inaccuracies and can often require complex user interaction.

Figure 8:
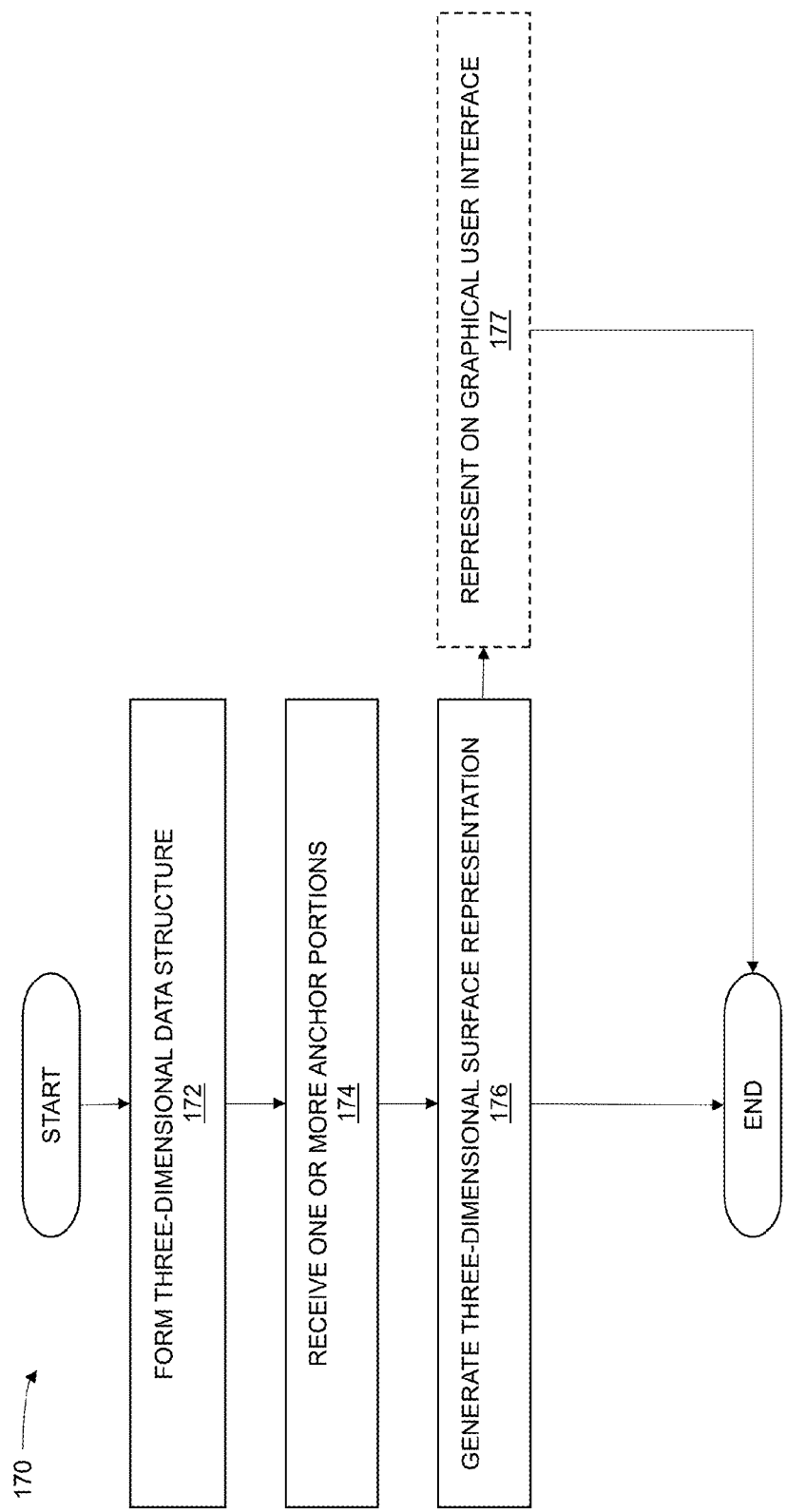
FIG. 8 is a flowchart of an exemplary method of representing a surface of a heart cavity of a patient.

FIG. 8 is a flowchart of an exemplary method 170 of representing a surface of a heart cavity of a patient. The exemplary method 170 can include forming 172 a three-dimensional data structure based on received locations of a tip section of a cardiac catheter in a heart cavity of a patient, receiving 174 identification of one or more anchor portions representing locations within the heart cavity, and generating 176 a three-dimensional surface representation of the heart cavity of the patient. The three-dimensional surface representation can be generated using information from the three-dimensional data structure and can be constrained relative to the one or more anchor portions. The tip section of the catheter can be, for example, the tip section 124 described with respect to FIGS. 2 and 3. Additionally, or alternatively, it should be appreciated that a heart cavity is an example of the anatomic structure 132. Accordingly, the tip section can interact with the heart cavity in any manner and form described herein with respect to the interaction of the tip section 124 and the anatomic structure 132.

Forming 172 the three-dimensional data structure can include any one or more of the various different methods of forming a three-dimensional data structure disclosed herein. For example, forming 172 the three-dimensional data structure can be analogous to forming 164 the three-dimensional data structure as described with respect to FIG. 7. Accordingly, forming 172 the three-dimensional data structure can be based on locations visited by the catheter in the heart cavity. Thus, in implementations in which the three-dimensional data structure includes a three-dimensional grid, voxels corresponding to visited locations of the catheter can be set to a different state than voxels corresponding to locations that have not been visited by the catheter.

In general, receiving 174 the one or more anchor portions on the three-dimensional data structure can be analogous to receiving 166 the one or more anchor portions on the three-dimensional data structure, as described with respect to FIG. 7. Thus, for example, receiving 174 the one or more anchor portions on the three-dimensional data structure can include receiving an input command from a user interface (e.g., an input device such as a keyboard, a mouse, a touchscreen, and the like) corresponding to a location of an anatomic feature and/or receiving a signal indicative of contact between the catheter and tissue in the heart cavity. In the case of the heart cavity, the one or more anchor portions can correspond, for example, to the location of one or more carina associated with the heart cavity. As a more specific example, the one or more anchor portions can correspond to a carina between the left atrial appendage (LAA) and the left superior pulmonary vein (LSPV).

In the alternative, or in addition, receiving 174 the one or more anchor portions can include receiving one or more signals corresponding to one or more respective locations of the cardiac catheter in the heart cavity. For example, the one or more signals corresponding to one or more respective locations of the cardiac catheter in the heart cavity can correspond to a blood-tissue boundary of the heart cavity. Such signals can include, for example, to one or more of: a change in an electric signal (e.g., electrogram or impedance) detected by one or more electrodes of the catheter, a force detected by a force sensor of the catheter, an ultrasound signal of an ultrasound sensor of the catheter, and a deformation of at least a portion of the catheter. For example, such signals can correspond to an amplitude derived from an electrogram detected by one or more electrodes of the medical device.

Generating 176 the three-dimensional surface representation of the heart cavity of the patient can be, in general, analogous to generating 167 the three-dimensional surface representation of the anatomic structure as described with respect to FIG. 7. Accordingly, it should be understood that generating 176 the three-dimensional surface representation of the heart cavity can be based, for example, on one or more of a "marching cubes" algorithm, a "ball-pivoting" algorithm, and a "power crust algorithm," with the algorithm or algorithms constrained relative to the one or more anchor portions. Further, or instead, generating 176 the three-dimensional surface representation of the heart cavity of the patient can include an undo function such that one or more of the anchor portions can be removed or repositioned, and the three-dimensional surface representation of the heart cavity can be regenerated based on the updated position of the one or more anchor portions.

In certain implementations, the three-dimensional surface representation of the heart cavity can be surface smoothed. It should be appreciated that such surface smoothing can produce changes to the three-dimensional surface representation and, in certain instances, can cause the three-dimensional surface representation to no longer fully contain the visited locations. Additionally, or alternatively, surface smoothing can produce changes to the three-dimensional surface representation that can cause the three-dimensional surface representation to no longer pass directly through the anchor portions. Surface-smoothing the three-dimensional surface representation can result in any one or more of the various different advantages described herein. For example, surface smoothing the three-dimensional surface representation can facilitate visualization of the position of the catheter relative to the three-dimensional surface representation, which can be useful for positioning the catheter during an ablation treatment applied to a surface of the heart cavity.

In some implementations, the exemplary method 170 can further include representing 177, on a graphical user interface, at least one of a two-dimensional projection of the three-dimensional data structure, the one or more anchor portions, and a two-dimensional projection of the three-dimensional surface representation. Representing 177 the two-dimensional projection of the three-dimensional surface representation and generating 176 the three-dimensional surface representation can be part of an iterative process, such as an iterative process analogous to the iterative process described with respect to the exemplary method 160.

The graphical user interface can be, for example, the graphical user interface 110 described with respect to FIG. 1. In certain implementations, the one or more anchor portions can be represented 177, on the graphical user interface, as annotations or other similar visual indicia on the three-dimensional surface representation of the heart cavity, on the three-dimensional data structure, or both. Additionally, or alternatively, the one or more anchor portions can be represented 177 on the graphical user interface independently of the three-dimensional surface representation, the three-dimensional data structure, or both. The annotations can, for example, be tags of certain anatomic features and/or tags related to the position of a treatment (such as a lesion created through tissue ablation).

While certain implementations have been described, other implementations are additionally or alternatively possible.

For example, while graphical user interfaces have been described as including a two-dimensional display, any one or more of the graphical user interfaces described herein can additionally, or alternatively, include a three-dimensional display. Examples of such a three-dimensional display include an augmented reality environment, a virtual reality environment, and combinations thereof.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals.

It will further be appreciated that a realization of the processes or devices described above may include computer-executable code created using a structured programming language such as C, an object oriented programming language such as C++, or any other high-level or low level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices.

In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A method comprising:
    receiving a plurality of location signals, each received location signal indicative of a respective location of a medical device in an anatomic structure of a patient;
    forming a three-dimensional data structure representing locations, within the anatomic structure, visited by the medical device at the locations corresponding to the plurality of location signals;
    receiving one or more anchor portions representing locations relative to the anatomic structure;
    generating a three-dimensional surface representation of the anatomic structure of the patient based only on the plurality of locations signals and the one or more anchor portions, wherein the three-dimensional surface representation of the anatomic structure of the patient is constrained to contain at least a portion of the three-dimensional data structure, and wherein generating the three-dimensional surface representation of the anatomic structure of the patient includes a volumetric smoothing, and further wherein the volumetric smoothing varies relative to the one or more anchor portions; and
    displaying, on a graphical user interface, at least one of a two-dimensional projection of the three-dimensional data structure, the one or more anchor portions, and a two-dimensional projection of the three-dimensional surface representation.

2. The method of claim 1, wherein receiving the one or more anchor portions representing locations relative to the anatomic structure includes receiving, from one or more sensors disposed on the medical device, a signal indicative of contact between the medical device and tissue of the anatomic structure.

3. The method of claim 2, wherein the signal indicative of contact is indicative of a blood-tissue boundary of the anatomic structure of the patient.

4. The method of claim 2, wherein the signal indicative of contact includes one or more of: a change in impedance detected by one or more electrodes of the medical device, a force detected by a force sensor of the medical device, an ultrasound signal of an ultrasound sensor of the medical device, a deformation of at least a portion of the medical device, and an amplitude derived from an electrogram detected by one or more electrodes of the medical device.

5. The method of claim 1, wherein receiving the one or more anchor portions includes receiving an input command from a user.

6. The method of claim 1, wherein receiving the one or more anchor portions includes identifying a subset of the three-dimensional data structure.

7. The method of claim 1, wherein receiving the one or more anchor portions includes receiving a respective confidence level associated with each of the one or more anchor portions, and constraining the three-dimensional surface representation relative to the one or more anchor portions is based on the respective confidence level associated with each of the one or more anchor portions.

8. The method of claim 1, further comprising representing, on the graphical user interface, the one or more anchor portions as annotations on the three-dimensional surface representation of the anatomic structure.

9. The method of claim 1, further comprising representing, on the graphical user interface, the one or more anchor portions as annotations on the three-dimensional data structure.

10. The method of claim 1, further comprising determining whether the one or more anchor portions have been modified and, based on whether the one or more anchor portions have been modified, repeating the generating step.

11. The method of claim 10, wherein determining whether the one or more anchor portions have been modified includes determining whether one or more of previously identified anchor portions have been removed.

12. The method of claim 1, wherein the three-dimensional surface representation of the anatomic structure is a continuous mesh.

13. A method, comprising:
    forming a three-dimensional data structure based on received locations of a tip section of a cardiac catheter in a heart cavity of a patient;
    receiving one or more anchor portions representing locations relative to the heart cavity, wherein receiving the one or more anchor portions comprises receiving a signal indicative of one or more of the following: a change in impedance detected by one or more electrodes of the cardiac catheter, a force detected by a force sensor of the cardiac catheter, a deformation of at least a portion of the cardiac catheter, and an amplitude derived from an electrogram detected by one or more electrodes of the cardiac catheter;
    generating a three-dimensional surface representation of the heart cavity of the patient based only on the received locations of the tip section of the cardiac catheter and on the received one or more anchor portions, wherein the three-dimensional surface representation of the heart cavity of the patient is constrained relative to the received one or more anchor portions and contains at least a portion of the three-dimensional data structure; and displaying, on a graphical user interface, a two-dimensional projection of the three-dimensional data structure, at least one of the received one or more anchor portions, and/or a two-dimensional projection of the generated three-dimensional surface representation.

14. The method of claim 13, wherein receiving the one or more anchor portions includes receiving one or more location signals indicative of one or more respective locations of the cardiac catheter in the heart cavity.

15. The method of claim 13, wherein receiving the one or more anchor portions includes receiving, from a sensor disposed on the cardiac catheter, a signal indicative of a blood-tissue boundary of the heart cavity of the patient.

16. The method of claim 13, wherein receiving the one or more anchor portions includes receiving an input command from a user interface.

17. The method of claim 13, further comprising representing, on the graphical user interface, the at least one of the received one or more anchor portions as annotations on the three-dimensional surface representation of the heart cavity.

18. A non-transitory, computer-readable storage medium having stored thereon computer executable instructions for causing one or more processors to:

receive a plurality of location signals, each received location signal indicative of a respective location of a medical device in an anatomic structure of a patient;

form a three-dimensional data structure representing volumes, within the anatomic structure, occupied by the medical device at the locations corresponding to the plurality of location signals;

receive one or more anchor portions representing a subset of the three-dimensional data structure;

generate a three-dimensional surface representation of the anatomic structure of the patient based only on the plurality of location signals and the one or more anchor portions, the three-dimensional surface representation of the anatomic structure of the patient constrained relative to the one or more anchor portions and containing at least a portion of the three-dimensional data structure; and display, on a graphical user interface, a two-dimensional projection of the three-dimensional data structure, at least one of the one or more anchor portions, and/or a two-dimensional projection of the generated three-dimensional surface representation.

\* \* \* \* \*

UNITED STATES PATENT AND TRADEMARK OFFICE
CERTIFICATE OF CORRECTION

PATENT NO. : 10,376,320 B2
APPLICATION NO. : 15/592815
DATED : August 13, 2019
INVENTOR(S) : Doron Harlev et al.

It is certified that error appears in the above-identified patent and that said Letters Patent is hereby corrected as shown below:

In the Specification

In Column 18, Lines 10-11, delete "that that" and insert -- that --, therefor.

Signed and Sealed this
Twenty-sixth Day of May, 2020

Andrei Iancu
*Director of the United States Patent and Trademark Office*